United States Patent
Garvey et al.

(10) Patent No.: US 6,936,627 B2
(45) Date of Patent: Aug. 30, 2005

(54) NITROSATED AND NITROSYLATED $H_2$ RECEPTOR ANTAGONIST COMPOUNDS, COMPOSITIONS AND METHODS OF USE

(75) Inventors: David S. Garvey, Dover, MA (US); L. Gordon Letts, Dover, MA (US); Chia-En Lin, Burlington, MA (US); Tiansheng Wang, Concord, MA (US)

(73) Assignee: NitroMed, Inc., Lexington, MA (US)

( * ) Notice: Subject to any disclaimer, the term of this patent is extended or adjusted under 35 U.S.C. 154(b) by 14 days.

(21) Appl. No.: 10/282,071

(22) Filed: Oct. 29, 2002

(65) Prior Publication Data

US 2003/0060492 A1 Mar. 27, 2003

Related U.S. Application Data

(62) Division of application No. 09/441,891, filed on Nov. 17, 1999, now Pat. No. 6,552,047.
(60) Provisional application No. 60/140,839, filed on Jun. 28, 1999, and provisional application No. 60/108,877, filed on Nov. 17, 1998.

(51) Int. Cl.[7] ............ C07D 233/56; C07D 277/28; C07D 307/52; A61K 31/341; A61K 31/4164
(52) U.S. Cl. ............ 514/365; 514/400; 514/471; 548/204; 548/205; 548/335.5; 548/336.1; 548/340; 549/451
(58) Field of Search ............... 548/204, 205, 548/335.5, 340, 336.1; 549/351, 451; 514/365, 400, 471

(56) References Cited

U.S. PATENT DOCUMENTS

| | | | |
|---|---|---|---|
| 3,950,333 | A | 4/1976 | Durant et al. |
| 4,279,906 | A | 7/1981 | Brown et al. |
| 4,705,683 | A | 11/1987 | Dettmar |
| 4,742,083 | A | 5/1988 | Richey |
| 4,900,741 | A | 2/1990 | Kohler |
| 5,037,815 | A | 8/1991 | Lukacsko et al. |
| 5,102,902 | A | 4/1992 | Mercer |
| 5,112,850 | A | 5/1992 | Benes et al. |
| 5,188,839 | A | 2/1993 | Pearmain |
| 5,229,134 | A | 7/1993 | Mention et al. |
| 5,403,830 | A | 4/1995 | Place |
| 5,407,688 | A | 4/1995 | Place |
| 5,476,669 | A | 12/1995 | Borody |
| 5,541,212 | A | 7/1996 | Bourinbaiar |
| 5,578,597 | A | 11/1996 | Spector et al. |
| 5,656,652 | A | 8/1997 | Davis |

FOREIGN PATENT DOCUMENTS

| | | |
|---|---|---|
| EP | 049618 | 4/1982 |
| EP | 224612 | 6/1987 |
| EP | 285681 | 10/1988 |
| EP | 743320 | 11/1996 |
| WO | 9407541 | 4/1994 |
| WO | 9733576 | 9/1997 |
| WO | 9857626 | 12/1998 |
| WO | 9944595 | 9/1999 |
| WO | 9945004 | 9/1999 |

OTHER PUBLICATIONS

Rice et al., Chemical Abstracts, 97:183, 1982.*
Montzka et al., Canadian Journal of Chemistry, 61(8), 1771–1777, 1983.*
DeFlora, Lancet, 2(8253), 993–994, 1981.*
Sekiguchi et al., *Arzneim. Forsch Drug Res.*, 43(1):134–138 (1993).
Ichikawa et al., *J. Pharmacol.*, 251:107–111 (1994).
Ivanov et al., *J. Pharmacol.*, 48:297–301 (1996).
Brunton, *Goodman and Gilman, The Pharmacological Basis of Therapeutics*, $9^{th}$ Edition, 901–915 (1996) McGraw–Hill.
Marazova et al., *Pharm. Pharmacol.*, 49:791–795 (1997).
Ichikawa et al., *Brit. J. Pharmacol.*, 122:1230–1236 (1997).
Sorba et al., *Arzneim. Forsch Drug Res.*, 47:849–854 (1997).
Sekine et al., *Chem. Pharm. Bull.*, 46:610–615 (1988).
Hirakawa et al., *Chem. Pharm. Bull.*, 46:610–622 (1988).
Hassan et al, *Analytica Chimica Acta*, 332:39–48 (1996).
Franekic et al, *Mutation Research*, 227:13–16 (1989).
International Search Report for PCT/US99/27207.
Maltz, *Clinical Bullein*, 9(4): 165–167 (1979).
Selker, *The New England Journal of Medicine*, 299 (15): 834 (1978).

* cited by examiner

*Primary Examiner*—Fiona T. Powers
(74) *Attorney, Agent, or Firm*—Wilmer Cutler Pickering Hale and Dorr LLP

(57) ABSTRACT

The invention describes novel nitrosated and/or nitrosylated $H_2$ receptor antagonist compounds, and novel compositions comprising at least one $H_2$ receptor antagonist compound that is optionally substituted with at least one NO and/or $NO_2$ group, and, optionally, at least one compound that donates, transfers or releases nitric oxide, stimulates endogenous synthesis of nitric oxide, elevates endogenous levels of endothelium-derived relaxing factor or is a substrate for nitric oxide synthase and/or at least one nonsteroidal anti-inflammatory drug, antacid, bismuth-containing reagent or anti-viral agent. The invention also describes methods for treating and/or preventing gastrointestinal disorders; improving gastroprotective properties of $H_2$ receptor antagonists; decreasing the recurrence of ulcers; facilitating ulcer healing; preventing and/or treating inflammations and microbial infections, ophthalmic diseases and disorders, multiple sclerosis, and viral infections; and decreasing or reducing the gastrointestinal toxicity associated with the use of nonsteroidal antiinflammatory compounds.

48 Claims, 7 Drawing Sheets

NITROSATED AND NITROSYLATED H$_2$ RECEPTOR ANTAGONIST COMPOUNDS, COMPOSITIONS AND METHODS OF USE

RELATED APPLICATIONS

This application is a divisional of U.S. application Ser. No. 09/441,891, filed Nov. 17, 1999, issued as U.S. Pat. No. 6,552,047, which claims priority under 35 USC §119 to U.S. application Ser. No. 60/108,877 filed Nov. 17, 1998 and to U.S. application Ser. No. 60/140,839 filed Jun. 28, 1999.

FIELD OF THE INVENTION

The invention describes novel nitrosated and/or nitrosylated H$_2$ receptor antagonist compounds, and novel compositions comprising at least one H$_2$ receptor antagonist compound that is optionally substituted with at least one NO and/or NO$_2$ group, and, optionally, at least one compound that donates, transfers or releases nitric oxide, stimulates endogenous synthesis of nitric oxide, elevates endogenous levels of endothelium-derived relaxing factor or is a substrate for nitric oxide synthase and/or at least one nonsteroidal antiinflammatory drug, antacid, bismuth-containing reagent or anti-viral agent. The invention also provides methods for treating and/or preventing gastrointestinal disorders; improving gastroprotective properties of H$_2$ receptor antagonists; decreasing the recurrence of ulcers; facilitating ulcer healing; treating and/or preventing inflammations and microbial infections, ophthalmic diseases and disorders, multiple sclerosis, and viral infections; and decreasing or reducing the gastrointestinal toxicity associated with the use of nonsteroidal antiinflammatory compounds.

BACKGROUND OF THE INVENTION

H$_2$ receptor antagonists are a well known class of drugs used in the management of gastrointestinal disorders. H$_2$ antagonists competitively inhibit the interaction of histamine with H$_2$ receptors. Although H$_2$ receptors are present in numerous tissues, including vascular and bronchial smooth muscle, they appear to have a minimal role in modulating physiological functions other than gastric secretion.

H$_2$ receptor antagonists inhibit gastric acid secretion elicited by histamine and other H$_2$ receptor agonists in a dose-dependent, competitive manner. The H$_2$ receptor antagonists also inhibit acid secretion elicited by gastrin and, to a lesser extent, by muscarinic agonists. H$_2$ receptor antagonists inhibit basal (fasting) and nocturnal acid secretion and that stimulated by food, sham feeding, fundic distention, and various pharmacological agents. The H$_2$ receptor antagonists reduce both the volume of gastric juice secreted and its hydrogen ion (H$^+$) concentration. Despite their good antisecretory properties, H$_2$ receptor antagonists are not unanimously recognized as gastroprotective agents. In addition, there is a high relapse rate associated with treating gastrointestinal disorders with H$_2$ receptor antagonists as they do not eliminate *Helicobacter pylori* (*Campylobacter pylori*), the bacteria responsible for peptic ulcer disease, gastric lymphoma and adenocarcinoma.

A variety of adverse reactions have been ascribed to H$_2$ receptor antagonists, such as cimetidine and ranitidine, reflecting, in part, the very large number of patients who have been treated with these drugs. The incidence of adverse reactions is low, and the adverse reactions are generally minor. The low incidence is attributable in part to the limited function of H$_2$ receptors in organs other than the stomach and to the poor penetration of these agents across the blood-brain barrier.

The most common side effects of H$_2$ receptor antagonists, such as cimetidine, are headache, dizziness, nausea, myalgia, skin rashes, and itching. The incidence of symptoms related to the central nervous system (CNS) appears to be higher in the elderly and in patients with impaired renal function. Loss of libido, impotence and gynecomastia are sometimes observed in patients who receive long-term therapy with high doses of H$_2$ receptor antagonists, such as cimetidine.

Sorba et al, *Arzneim-Forsch Drug Res.*, 47(II):849–854 (1997), the disclosure of which is incorporated by reference herein in its entirety, have developed a drug that combines a H$_2$ receptor antagonist with a nitric oxide (NO)-donor furoxan moiety. This drug is reported to retain weaker H$_2$ receptor antagonist activity relative to the parent drug but shows a NO-dependent gastroprotective effect.

U.S. Pat. No. 5,403,830, the disclosure of which is incorporated by reference herein in its entirety, describes pharmaceutical compositions and methods of treating gastrointestinal disorders by administering bismuth-containing agents in conjunction with a H$_2$ receptor antagonist. U.S. Pat. Nos. 5,403,830, and 5,407,688, and Ivnov et al, *J. Pharm. Pharmacol.*, 48:297–301 (1996) and Marazova et al, *J. Pharm. Pharmacol.*, 49:791–795 (1997), the disclosures of each of which are incorporated by reference herein in their entirety, describe treating or preventing gastrointestinal disorders by administering bismuth containing agents. U.S. Pat. Nos. 4,705,683, 4,900,741, 5,112,850 and 5,656,652, the disclosures of which are incorporated by reference herein in their entirety, describe administering H$_2$ receptor antagonists with polyacrylates, antimuscarinic agents, trapencine and antacids, respectively. U.S. Pat. No. 5,656,652, the disclosure of which is incorporated by reference herein in its entirety, describes the use of H$_2$ antagonists and antacids for the treatment of gastrointestinal disorders.

The administration of NSAIDs, such as indomethacin or ibuprofen, with H$_2$ receptor antagonists, such as cimetidine, is described in U.S. Pat. Nos. 5,037,815 and 4,279,906 and in WO 94/07541, the disclosure of each of which is incorporated by reference herein in its entirety. U.S. Pat. Nos. 5,102,902, 5,541,212 and 5,578,597, the disclosures of each of which are incorporated by reference herein in their entirety, disclose the use of H$_2$ receptor antagonists for treating multiple sclerosis and retrovirus infections.

There is a need in the art for H$_2$ receptor antagonist compounds that have gastroprotective properties, decrease the recurrence of ulcers, facilitate ulcer healing and that can be used at low dosages. The invention is directed to these, as well as other, important ends.

SUMMARY OF THE INVENTION

The invention provides compounds comprising a H$_2$ receptor antagonist to which is linked at least one NO and/or NO$_2$ group (i.e., nitrosylated and/or nitrosated). The H$_2$ receptor antagonists can be, for example, histamine analogs that contain a bulky side chain instead of an ethylamine moiety and retain the imidazole ring of histidine, such as cimetidine. The imidazole ring can be replaced by a furan (e.g., rantidine) or a thiazole (e.g., famotidine, nizatidine). The H$_2$ receptor antagonists can also be, for example, amide derivatives, such as, for example, roxatidine or a guanidino derivative, such as, for example, ebrotidine or famotidine. The invention also provides compositions comprising such compounds in a pharmaceutically acceptable carrier.

Another aspect of the invention provides compositions comprising at least one $H_2$ receptor antagonist, that is optionally substituted with at least one NO and/or $NO_2$ group (i.e., nitrosylated and/or nitrosated), and at least one compound that donates, transfers or releases nitric oxide and/or stimulates endogenous production of nitric oxide (NO) or endothelium-derived relaxing factor (EDRF) in vivo and/or is a substrate for nitric oxide synthase.

Yet another aspect of the invention provides methods for treating gastrointestinal disorders, improving the gastroprotective properties of $H_2$ receptor antagonists, increasing the rate of ulcer healing, decreasing the rate of recurrence of ulcers, treating inflammations, treating ophthalmic diseases and disorders, and treating microbial infections in a patient in need thereof which comprises administering to the patient at least one $H_2$ receptor antagonist compound, that is optionally substituted with at least one NO and/or $NO_2$ group (i.e., nitrosylated and/or nitrosated), and, optionally, at least one compound that donates, transfers or releases nitric oxide and/or stimulates endogenous production of NO or EDRF in vivo and/or is a substrate for nitric oxide synthase. The $H_2$ receptor antagonist that is optionally linked to at least one NO and/or $NO_2$ group and nitric oxide donor can be administered separately or as components of the same composition.

The invention also describes methods to decrease or reverse gastrointestinal toxicity and facilitate ulcer healing resulting from the administration of nonsteroidal antiinflammatory drugs (NSAIDs); methods to improve the gastroprotective properties, anti-*Helicobacter* properties and antacid properties of $H_2$ receptor antagonists; methods for preventing or treating gastrointestinal disorders; methods for treating multiple sclerosis; methods for treating ophthalmic diseases and disorders; and methods for treating viral infections, such as HIV disease. The nitrosated and/or nitrosylated NSAID and nitric oxide donor can be administered separately or as components of the same composition. These and other aspects of the are explained in detail herein.

DETAILED DESCRIPTION OF THE INVENTION

Figure 1:
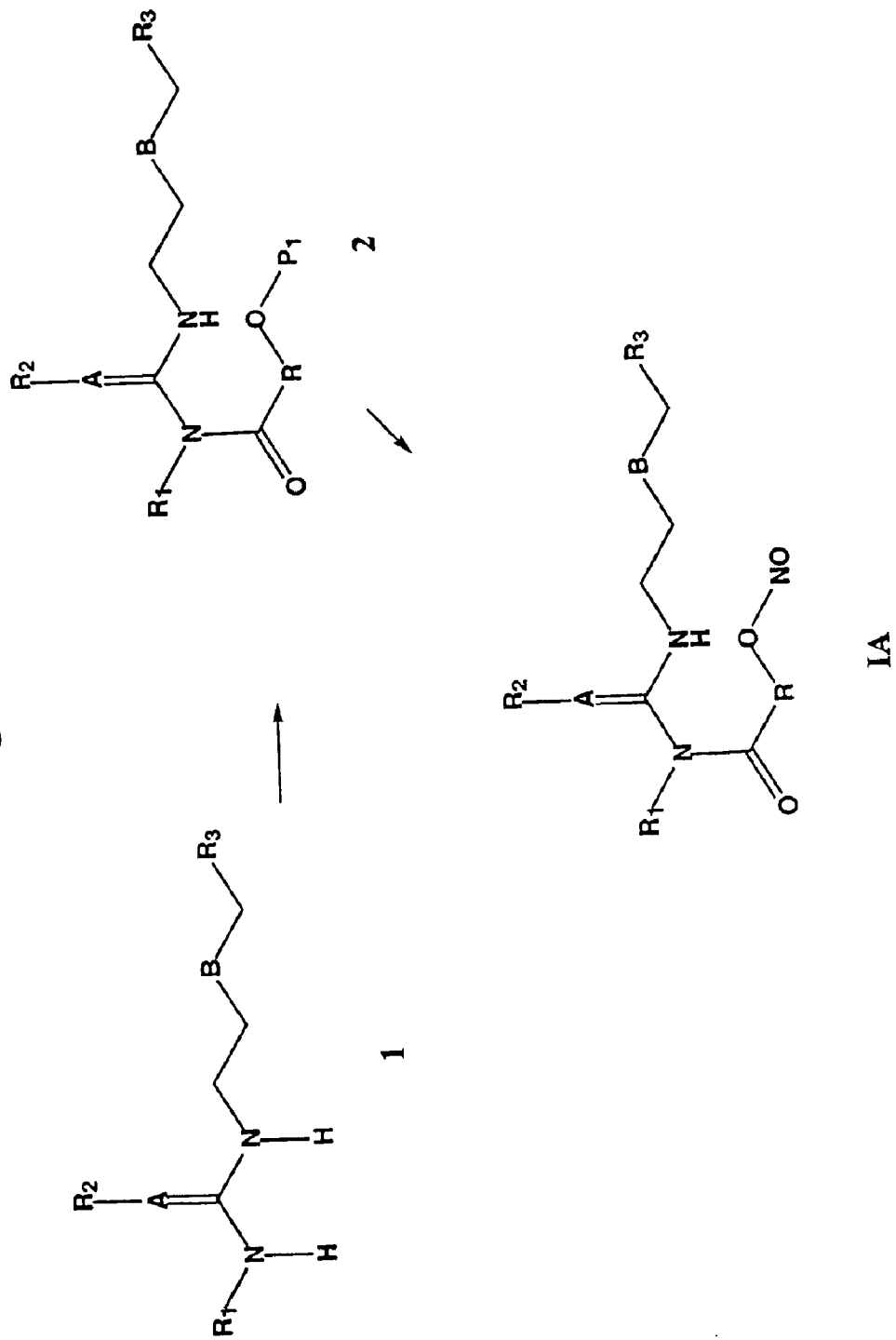
FIG. 1 is the synthetic scheme for the preparation of nitrite-containing guanidino derivatives of the compound of formula (I).

As used throughout the disclosure, the following terms, unless otherwise indicated, shall be understood to have the following meanings.

"Gastrointestinal disorder" refers to any disease or disorder of the upper gastrointestinal tract of a patient including, for example, peptic ulcers, stress ulcers, gastric hyperacidity, dyspepsia, gastroparesis, Zollinger-Ellison syndrome, gastroesophageal reflux disease, short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns.

"Upper gastrointestinal tract" refers to the esophagus, the stomach, the duodenum and the jejunum.

"Ulcers" refers to lesions of the upper gastrointestinal tract lining that are characterized by loss of tissue. Such ulcers include gastric ulcers, duodenal ulcers and gastritis.

"$H_2$ receptor antagonist" refers to any compound that reversibly or irreversibly blocks the activation of any $H_2$ receptor.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Patient" refers to animals, preferably mammals, more preferably humans.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO^-$, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0) octane, 7-oxabycyclo(2.2.1)heptyl, 8-azabicyclo(3,2,1)oct-2-enyl and the like "Cycloalkyl" refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamido, alkylcarboxamido, arylcarboxamido, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3, 5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to —O$^-$R$_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Amino" refers to —NH$_2$.

"Nitrate" refers to —O—NO$_2$.

"Nitrite" refers to —O—NO.

"Thionitrate" refers to —S—NO$_2$.

"Thionitrite" and "nitrosothiol" refer to —S—NO.

"Nitro" refers to the group —NO$_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{52}R_{53}N$—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino" refers to $R_{52}R_{55}N$—, wherein $R_{52}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Thio" refers to —S—.

"Sulfinyl" refers to —S(O)—.

"Methanthial" refers to —C(S)—.

"Thial" refers to =S.

"Sulfonyl" refers to —S(O)$_2$$^-$.

"Sulfonic acid" refers to —S(O)$_2$OR$_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to —S(O)$_2$OR$_{58}$, wherein $R_{58}$ is an alkyl group, an aryl group, an alkylaryl group or an aryl heterocyclic ring, as defined herein.

"Sulfonamido" refers to —S(O)$_2$—N(R$_{51}$)(R$_{57}$), wherein $R_{51}$ and $R_{57}$ are each independently a hydrogen atom, an alkyl group, an aryl group, an alkylaryl group, or an aryl-heterocyclic ring, as defined herein, and $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S$—, wherein $R_{50}$ is an alkyl group, as defined herein.

"Arylthio" refers to $R_{55}S$—, wherein $R_{55}$ is an aryl group, as defined herein.

"Alkylsulfinyl" refers to $R_{50}$—S(O)—, wherein $R_{50}$ is an alkyl group, as defined herein.

"Alkylsulfonyl" refers to $R_{50}$—S(O)$_2$—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—S(O)$_2$—, wherein $R_{55}$ is an aryl group, as defined herein.

"Amidyl" refers to $R_{51}C(O)N(R_{57})$— wherein $R_{51}$ and $R_{57}$ are each independently a hydrogen atom, an alkyl group, an aryl group, an alkylaryl group, or an arylheterocyclic ring, as defined herein.

"Ester" refers to $R_{51}C(O)O$— wherein $R_{51}$ is a hydrogen atom, an alkyl group, an aryl group, an alkylaryl group, or an arylheterocyclic ring, as defined herein.

"Carbamoyl" refers to —O—C(O)N(R$_{51}$)(R$_{57}$), wherein $R_{51}$ and $R_{57}$ are each independently a hydrogen atom, an alkyl group, an aryl group, an alkylaryl group or an aryl-heterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)OR$_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Carboxylic ester" refers to —C(O)O$R_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group, an alkylaryl group or an aryl-heterocyclic ring, as defined herein, and $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{58}$)—C(O)N($R_{51}$)($R_{57}$) wherein $R_{51}$, $R_{57}$, and $R_{58}$ are each independently a hydrogen atom, an alkyl group, an aryl group, an alkylaryl group, or an arylheterocyclic ring, as defined herein, or $R_{51}$ and $R_{57}$ taken together are a heterocyclic ring, a cycloalkyl group or a bridged cycloalkyl group, as defined herein.

Compounds that donate, transfer or release nitric oxide species in vivo have been recognized as having a wide spectrum of advantages and applications. The invention is based on the unexpected discovery of the effects of such compounds alone and together with one or more $H_2$ receptor antagonists and/or one or more $H_2$ receptor antagonists directly or indirectly linked with one or more nitric oxide moieties. Treatment or prevention of gastrointestinal disorders, improved gastroprotective properties, decreased rate of recurrence of ulcers (preferably peptic ulcers), faster ulcer healing, treatment of inflammations, treatment of ophthalmic diseases and disorders and treatment of microbial infections can be obtained by the use of the nitrosated and/or nitrosylated $H_2$ receptor antagonists of the invention; or by the use of the nitrosated and/or nitrosylated $H_2$ receptor antagonists in conjunction with one or more compounds that donate, release or transfer nitric oxide and/or stimulate endogenous production of NO and/or EDRF in vivo and/or is a substrate for nitric oxide synthase.

The invention is also based on the discovery that it is possible to administer at least one $H_2$ receptor antagonist, optionally linked to at least one NO and/or $NO_2$ group, and at least one nitric oxide donor to treat gastrointestinal disorders, improve gastroprotective properties, decrease the rate of recurrence of peptic ulcers and increase the rate of ulcer healing of $H_2$ receptor antagonists, to treat inflammations and microbial infections, and to treat ophthalmic diseases and disorders. $H_2$ receptor antagonists are compounds that competitively inhibit the interaction of histamine with $H_2$ receptors. A nitric oxide donor is a compound that contains a nitric oxide moiety and releases or chemically transfers nitric oxide to another molecule, as defined herein.

The compounds and compositions of the invention are novel and can be used to treat numerous gastrointestinal disorders, inflammations, microbial infections and ophthalmic diseases and disorders. Such gastrointestinal disorders include, for example, peptic ulcers, stress ulcers, gastric hyperacidity, dyspepsia, gastroparesis, Zollinger-Ellison syndrome, gastroesophageal reflux disease, short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. Such inflammations and/or microbial infections include, for example, inflammations and/or infections of the eyes, ears, nose, and/or skin. Such ophthalmic diseases and disorders include, for example, glaucoma, inflammation of the eye and elevation of intraocular pressure. The compounds and compositions of the invention can also be used as a pre-anesthetic medication in emergency operations to reduce the danger of aspiration of acidic gastric contents The $H_2$ receptor antagonist compounds that are nitrosated and/or nitrosylated in accordance with the invention and/or are included in the compositions of the invention can be any of those known in the art, including those exemplified below.

Cimetidine (marketed under the trade name TAGAMET® by SmithKline Beecham Pharmaceuticals, Philadelphia, Pa.) is one of the most widely used anti-secretory agents in the treatment of gastric ulcers. This compound blocks the histamine receptors within the stomach mucosa, thereby preventing histamine molecules from signaling the stomach cells to secrete acid. $H_2$ receptor blocking agents that are more potent than cimetidine (e.g. ranitidine, nizatidine) are also widely used. Although the $H_2$ receptor blocking antisecretory agents are effective in treating gastrointestinal disorders, they do not have any gastroprotective properties and, in addition, there is a high recurrence of ulcers associated with their use.

Another group of $H_2$ receptor antagonists are amide derivatives, which include, for example, roxatidine.

Yet another group of $H_2$ receptor antagonists are guanidino derivatives, which include, for example, famotidine and ebrotidine.

Other $H_2$ receptor antagonists contemplated by the invention include burimamide, metiamide, tiotidine and oxmetidine.

Each of the above contemplated $H_2$ receptor antagonists is described more fully in the literature, such as in Goodman and Gilman, The Pharmacological Basis of Therapeutics (9th Edition), McGraw-Hill, 1995, Pgs. 901–915; the Merck Index on CD-ROM, Twelfth Edition, Version 12:1, 1996.

In one embodiment, the invention describes nitrosated and/or nitrosylated compounds of Formula (I):

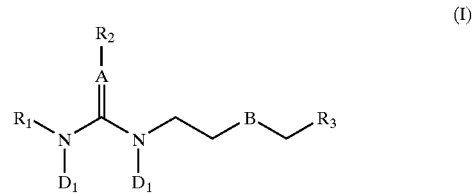

(I)

wherein

A is CH, nitrogen or sulfur;

B is oxygen, S(O)$_o$ or $CH_2$;

o is an integer from 0 to 2;

$D_1$ is a hydrogen atom or D;

$R_1$ is a hydrogen atom, a lower alkyl group, a cycloalkylalkyl group, a hydroxyalkyl group, an alkoxyalkyl group or an aminoalkyl group;

$R_2$ is a lone pair of electrons, a nitrile group, a nitro group, an alkylsulfonyl group, an arylsulfonyl group, an alkylcarbonyl group, a carboxamido group, a carboxylic ester or a cycloalkylalkyl group;

$R_3$ is:

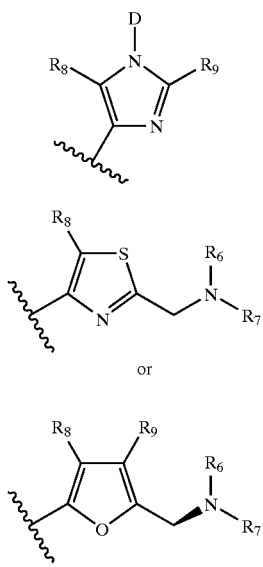

with the proviso that at least one $D_1$ must be D if there is no D designated in the structure;

$R_6$ and $R_7$ are each independently K, a hydrogen atom, a lower alkyl group, an alkylaryl group, an arylcarbonyl group, an alkylcarbonyl group, or $R_6$ and $R_7$ taken together with the nitrogen atom to which they are attached are a heterocyclic ring;

$R_8$ and $R_9$ are independently a hydrogen atom or a lower alkyl group;

D is Q or K;

Q is —NO or —NO$_2$;

K is -$W_a$-$E_b$-$(C(R_e)(R_f))_p$-$E_c$-$(C(R_e)(R_f))_x$-$W_d$-$(C(R_e)(R_f))_y$-$W_t$-$E_f$-$W_g$—$(C(R_e)(R_f))_z$-T-Q;

a, b, c, d, g, i and j are each independently an integer from 0 to 3;

p, x, y and z are each independently an integer from 0 to 10;

W at each occurrence is independently —C(O)—, —C(S)—, -T-, —$(C(R_e)(R_f))_h$—, an alkyl group, an aryl group, a heterocyclic ring, an arylheterocyclic ring, or —(CH$_2$CH$_2$O)$_q$—;

E at each occurrence is independently -T-, an alkyl group, an aryl group, —$(C(R_e)(R_f))_h$—, a heterocyclic ring, an arylheterocyclic ring, or —(CH$_2$CH$_2$O)$_q$—;

h is an integer form 1 to 10;

q is an integer of from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a carbamoyl, a urea, a nitro, -T-Q, or $(C(R_e)(R_f))_k$-T-Q, or $R_e$ and $R_f$ taken together with the carbon atom to which they are attached are a carbonyl, a methanthial, a heterocyclic ring, a cycloalkyl group or a bridged cycloalkyl group;

k is an integer from 1 to 3;

T at each occurrence is independently a covalent bond, a carbonyl, an oxygen, —S(O)$_o$— or —N(R$_a$)R$_i$—;

o is an integer from 0 to 2;

$R_a$ is a lone pair of electrons, a hydrogen or an alkyl group;

$R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T-Q)(R$_e$)(R$_f$), or —(N$_2$O$_2$—)$^-$.M$^+$, wherein M$^+$ is an organic or inorganic cation; with the proviso that when $R_i$ is —CH$_2$—C(T-Q)(R$_e$)(R$_f$) or —(N$_2$O$_2$)$^-$.M$^+$, or $R_e$ or $R_f$ are T-Q or $(C(R_e)(R_f))_k$-T-Q, then the "-T-Q" subgroup designated in X can be a hydrogen, an alkyl, an alkoxy, an alkoxyalkyl, an aminoalkyl, a hydroxy, a heterocyclic ring or an aryl group.

In cases where $R_e$ and $R_f$ are a heterocyclic ring or taken together $R_e$ and $R_f$ are a heterocyclic ring, then $R_i$ can be a substituent on any disubstituted nitrogen contained within the radical where $R_i$ is as defined herein.

In cases where multiple designations of variables which reside in sequence are chosen as a "covalent bond" or the integer chosen is 0, the intent is to denote a single covalent bond connecting one radical to another. For example, E$_0$ would denote a covalent bond, while E$_2$ denotes (E—E) and $(C(R_e)(R_f))_2$ denotes —C(R$_e$)(R$_f$)—C(R$_e$)(R$_f$)—.

Another embodiment of the invention describes compounds of the Formula (II):

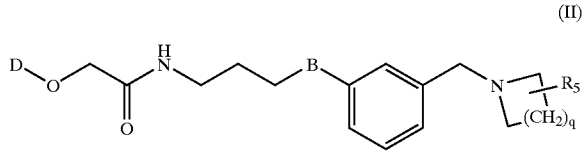

wherein $R_5$ is a hydrogen atom, a hydroxy group or a hydroxyalkyl group; and q, B and D are as defined herein.

Another embodiment of the invention describes compounds of Formula (III):

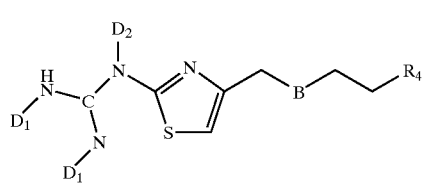

(III)

wherein
D$_2$ is D$_1$ or a lone pair of electrons;
R$_4$ is:

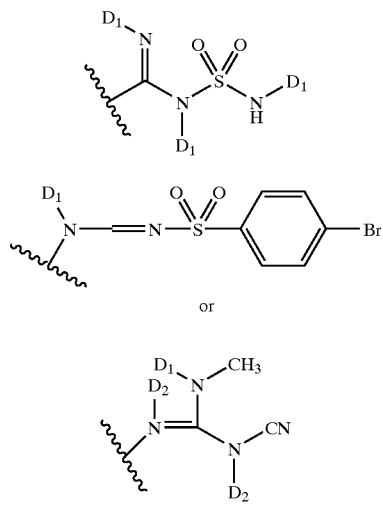

B, D and D$_1$ are as defined herein, with the proviso that at least one D$_1$ must be D, and D is as defined herein.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The invention includes within its scope all such isomers and mixtures thereof.

The invention includes within its scope compounds which may exist in more than one resonance form and the effect that may have on the positions at D$_1$ substituents designated in the above structures. The invention also includes within its scope the regiomers of the double bonds of the substituted guanidino or amidino groups.

Another aspect of the invention provides processes for making the novel compounds of the invention and to the intermediates useful in such processes. The compounds of Formulas (I), (II) and (III) can be synthesized by one skilled in the art following the methods and examples described herein. For example, the compounds of the invention can be synthesized as shown in FIGS. 1–6, in which A, B, D, D$_1$, E, K, Q, T, W, R$_1$, R$_2$, R$_3$, R$_4$, R$_5$, R$_6$, R$_7$, R$_8$, R$_9$, R$_e$, R$_f$, a, b, c, d, g, i, j, p, q, x, y and z are as defined herein or as depicted in the reaction schemes for Formulas (I)–(III); P$^1$ is an oxygen protecting group; and P$^2$ is a sulfur protecting group. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, John Wiley & Sons, New York (1991).

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Nitroso compounds of formula (I), wherein R$_1$, R$_2$, R$_3$, R$_6$, R$_7$, R$_8$ and R$_9$ are as defined herein, and a nitrite containing acyl group is representative of the D$_1$ group as defined herein can be prepared as outlined in FIG. 1. The synthesis of acylated prodrugs of substituted guanidines is well known in the art. Patent Application EP 743320 and PCT Patent Application WO 97/33576, the disclosures of each of which are incorporated by reference herein in their entirety, describe the preparation of acylguanidine and acylamidine derivatives as thrombin inhibitor prodrugs. The guanidino derivative of structure 1 is converted to the acylated guanidino derivative of structure 2 wherein R is -W$_{a-1}$-E$_b$-(C(R$_e$)(R$_f$))$_p$-E$_c$-(C(R$_e$)(R$_f$))$_x$-W$_d$-(C(R$_e$)(R$_f$))$_y$-W$_i$-E$_j$-W$_{g-(C(Re)(R_f))_z}$-T-Q by reaction with an appropriate protected alcohol containing acid wherein P$^1$ is as defined herein. Preferred methods for the preparation of acylated guanidino derivatives are initially forming the mixed anhydride via reaction of the protected alcohol containing acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the guanidino derivative, preferably in the presence of a condensation catalyst, such as 4-dimethyl-amino pyridine (DMAP). Alternatively, the protected alcohol containing acid can first be converted to the acid chloride by treatment with oxalyl chloride in the presence of a catalytic amount of DMF. The acid chloride is then reacted with the guanidino derivative, preferably in the presence of a condensation catalyst, such as DMAP, and a tertiary amine base, such as triethylamine, to produce the acylated guanidino derivative. Alternatively, the protected alcohol containing acid can be coupled to produce the acylated guanidino derivative by treatment with a dehydration agent, such as dicyclohexyl-carbodiimide (DCC) or 1-(3-dimethylaminopropyl)-3-ethylcarbodiimide hydrochloride (EDC), with a condensation catalyst, such as DMAP. Alternatively the acylating agent may be reacted with the preformed anion of the guanidino functionality prepared by deprotonating the guanidino group with a strong base such as sodium hydride, lithium hexamethyldisilazide or potassium t-butoxide in an inert solvent such as THF. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent, such as thionyl chloride nitrite, thionyl dinitrite or nitrosium tetrafluoroborate, in a suitable anhydrous solvent, such as dichloromethane, THF, DMF or acetonitrile, with or without an amine base, such as pyridine or triethylamine, produces the compounds of structure IA.

Figure 2:
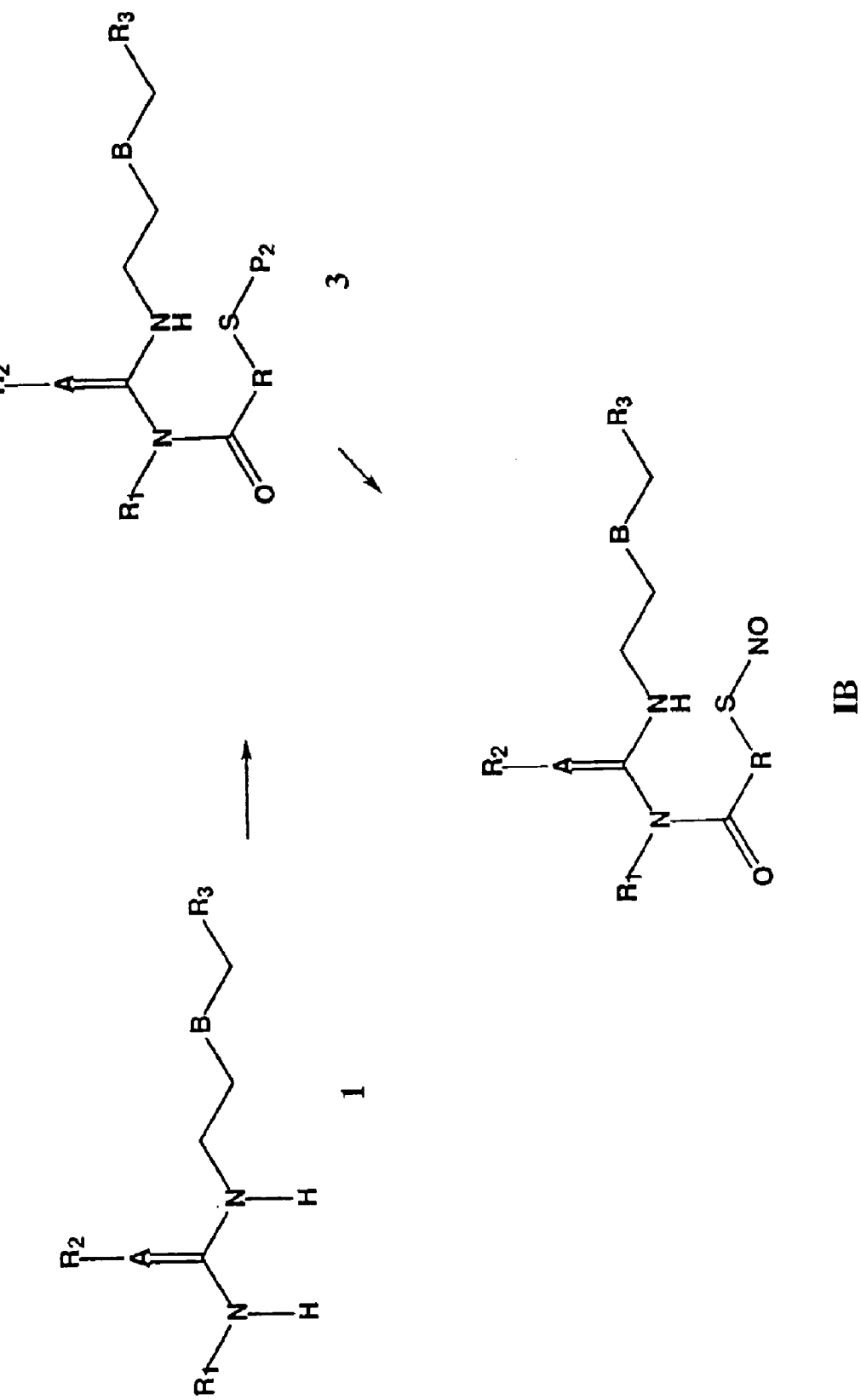
FIG. 2 is the synthetic scheme for the preparation of a nitrosothiol-containing guanidino derivatives of the compound of formula (II).

Nitroso compounds of formula (I) wherein $R_1$, $R_2$, $R_3$, $R_6$, $R_7$, $R_8$ and $R_9$ are as defined herein and a nitrosothiol containing acyl group is representative of the $D_1$ group as defined herein can be prepared as outlined in FIG. 2. The guanidino derivative group of structure 1 is converted to the acylated guanidino derivative of structure 3 by reaction with an appropriate protected thiol containing acid wherein R and $P^2$ are as defined herein. Preferred methods for the preparation of acylated guanidino derivatives are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the guanidino derivative, preferably in the presence of a condensation catalyst, such as DMAP. Alternatively, the acid can first be converted to the acid chloride by treatment with oxalyl chloride in the presence of a catalytic amount of DMF. The acid chloride is then reacted with the guanidino derivative preferably in the presence of a condensation catalyst, such as DMAP, and a tertiary amine base, such as triethylamine, to produce the acylated guanidino derivative. Alternatively, the protected thiol containing acid and guanidino derivative can be coupled to produce the acylated guanidino derivative by treatment with a dehydration agent, such as DCC or EDC, with a condensation catalyst, such as DMAP. Alternatively the acylating agent may be reacted with the preformed anion of the guanidino functionality prepared by deprotonating the guanidino group with a strong base such as sodium hydride, lithium hexamethyldisilazide or potassium t-butoxide in an inert solvent such as THF. Preferred protecting groups for the thiol moiety are as a thioester, such as thioacetate or thiobenzoate, as a disulfide, as a thiocarbamate, such as N-methoxy-methyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenyl-phosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure IB. Alternatively, a stoichiometric quantity of sodium nitrite in alcoholic or aqueous acid produces the compounds of structure IB.

Figure 3:
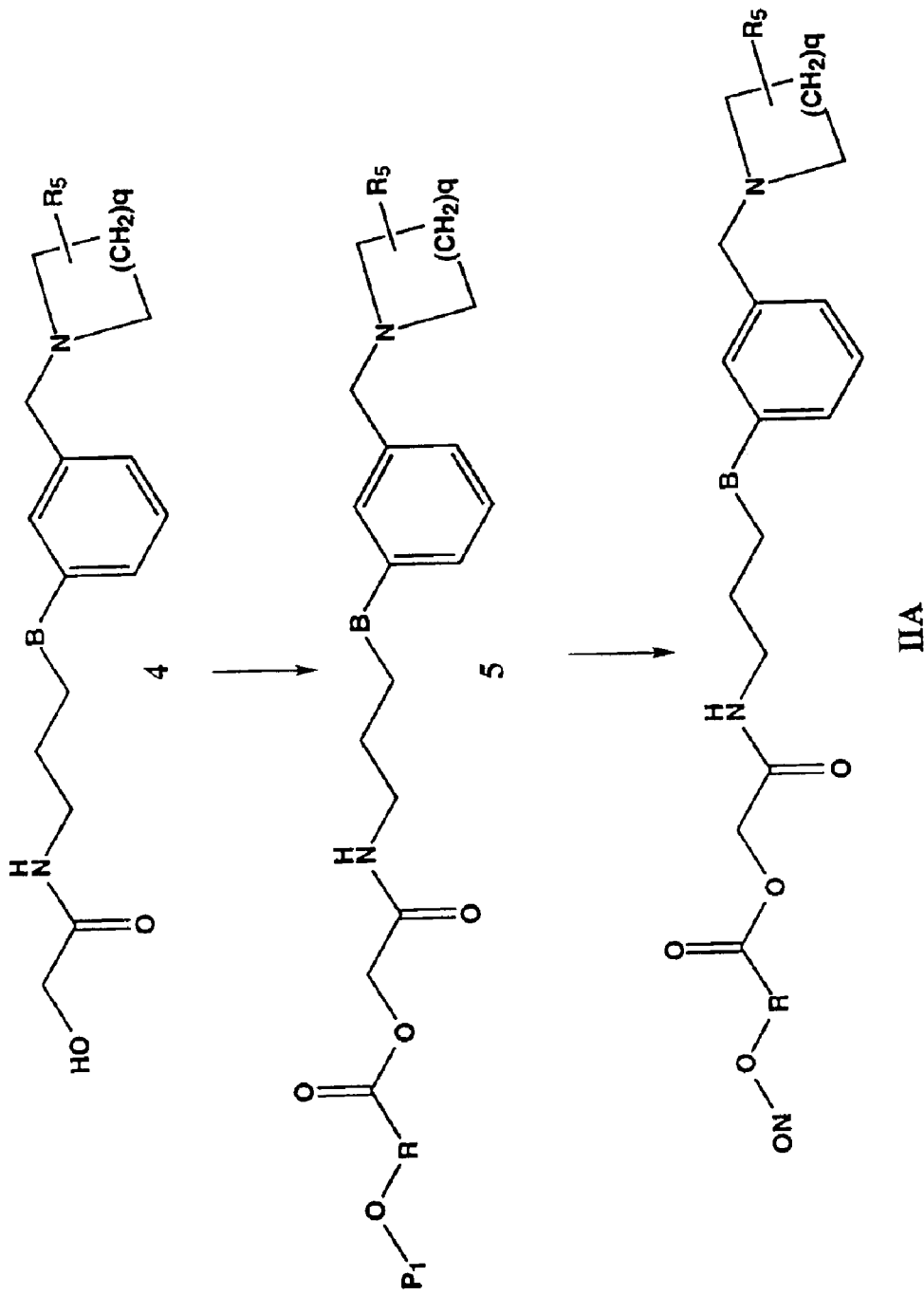
FIG. 3 is the synthetic scheme for the preparation of nitrite derivatives of the compound of formula (II).

Nitroso compounds of formula (II) wherein B, $R_5$ and q are as defined herein and a nitrite containing acyl group is representative of the D group as defined herein can be prepared as outlined in FIG. 3. The alcohol of structure 4 is converted to the ester of structure 5 by reaction with an appropriate protected alcohol containing acid wherein R and $P^1$ are as defined herein. Preferred methods for the preparation of esters are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the alcohol, preferably in the presence of a condensation catalyst, such as DMAP. Alternatively, the acid can first be converted to the acid chloride by treatment with oxalyl chloride in the presence of a catalytic amount of DMF. The acid chloride is then reacted with the hydroxyl group, preferably in the presence of a condensation catalyst, such as DMAP, and a tertiary amine base, such as triethylamine, to produce the ester. Alternatively, the protected alcohol containing acid can be coupled to produce the ester by treatment with a dehydration agent, such as DCC or EDC, with or without a condensation catalyst, such as DMAP. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent, such as thionyl chloride nitrite, thionyl dinitrite or nitrosium tetrafluoroborate, in a suitable anhydrous solvent, such as dichloromethane, THF, DMF or acetonitrile, with or without an amine base, such as pyridine or triethylamine, produces the compounds of formula IIA.

Figure 4:
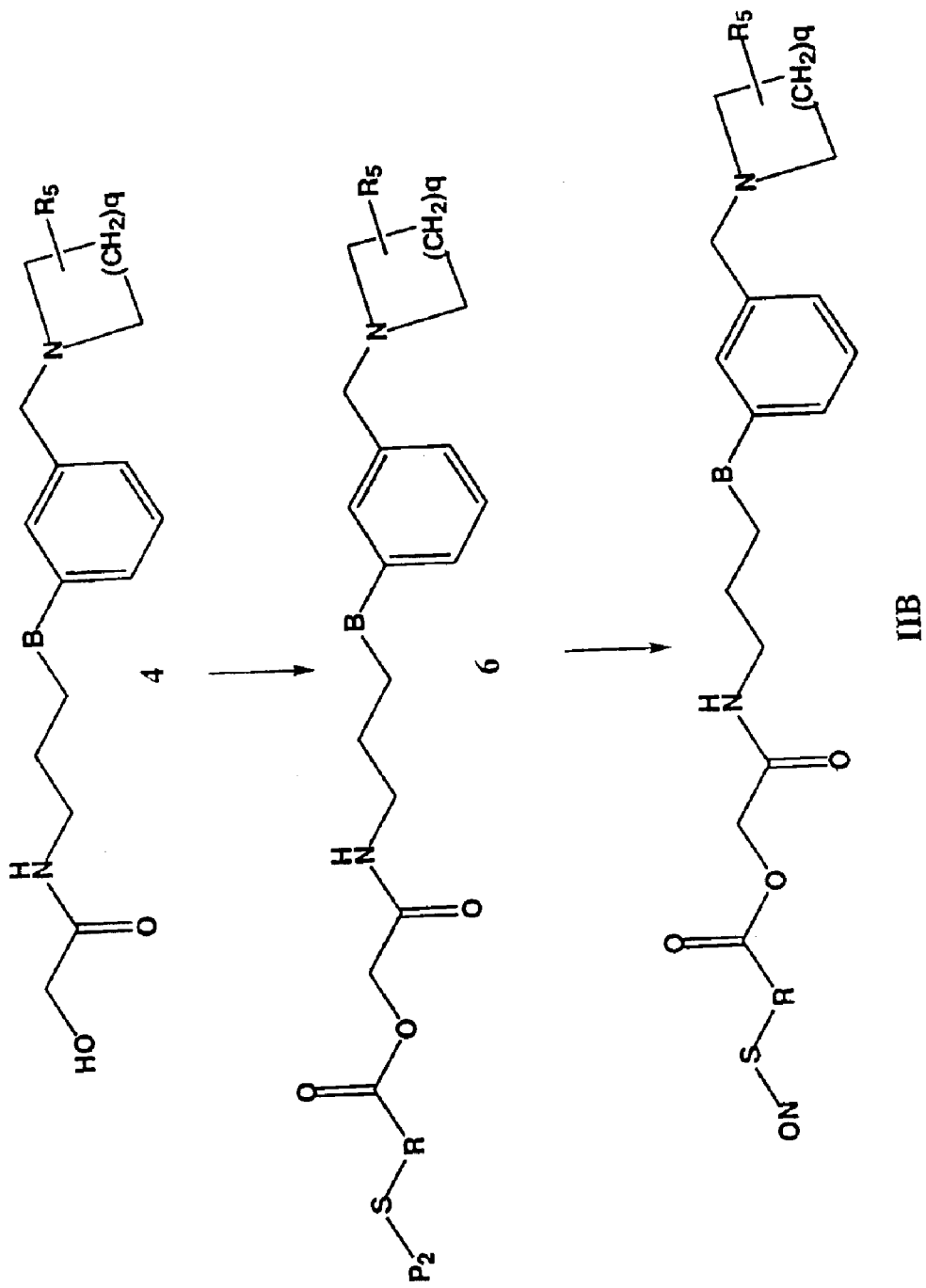
FIG. 4 is the synthetic scheme for the preparation of nitrosothiol derivatives of the compound of formula (II).

Nitroso compounds of formula (II) wherein B, $R_5$ and q are as defined herein and a nitrosothiol containing acyl group is representative of the D group as defined herein can be prepared as outlined in FIG. 4. The alcohol of structure 4 is converted to the ester of structure 6 by reaction with an appropriate protected thiol containing acid wherein R and $P^2$ are as defined herein. Preferred methods for the preparation of esters are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the hydroxyl group, preferably in the presence of a condensation catalyst, such as DMAP. Alternatively, the acid can first be converted to the acid chloride by treatment with oxalyl chloride in the presence of a catalytic amount of DMF. The acid chloride is then reacted with the hydroxyl moiety, preferably in the presence of a condensation catalyst, such as DMAP, and a tertiary amine base, such as triethylamine, to produce the ester. Alternatively, the protected thiol containing acid and alcohol can be coupled to produce the ester by treatment with a dehydration agent, such as DCC or EDC with or without a condensation catalyst such as DMAP. Preferred protecting groups for the thiol moiety are as a disulfide, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenyl-phosphine in water and sodium borohydride are preferred methods for reducing disulfide groups while mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure IIB. Alternatively, a stoichiometric quantity of sodium nitrite in alcoholic or aqueous acid produces the compounds of structure IIB.

Figure 5:
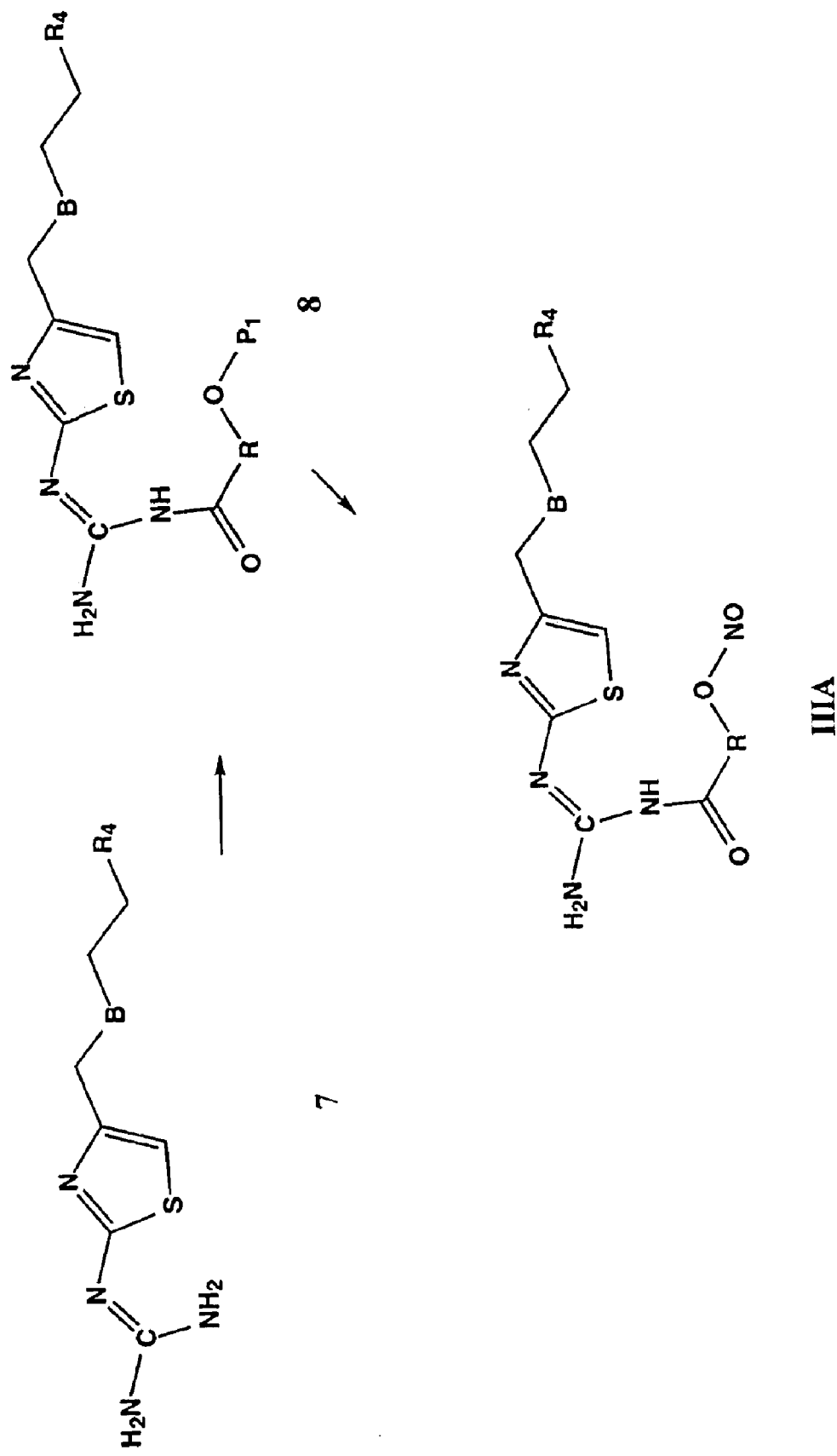
FIG. 5 is the synthetic scheme for the preparation of nitrite-containing guanidino derivatives of the compound of formula (III).

Nitroso compounds of formula (III) wherein B and $R_4$ are as defined herein and a nitrite containing acyl group is representative of the $D_1$ group as defined herein can be prepared as outlined in FIG. 5. The guanidino derivative of formula 7 is converted to the acylated guanidino derivative of structure 8 by reaction with an appropriate protected alcohol containing acid wherein R and $P^1$ are as defined herein. Preferred methods for the preparation of acylated guanidino derivatives are initially forming the mixed anhydride via reaction of the protected alcohol containing acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the guanidino derivative, preferably in the presence of a condensation catalyst, such as DMAP. Alternatively, the protected alcohol containing acid can first be converted to the acid chloride by treatment with oxalyl chloride in the presence of a catalytic amount of DMF. The acid chloride is then reacted with the guanidino derivative, preferably in the presence of a condensation catalyst, such as DMAP, and a tertiary amine base, such as triethylamine, to produce the acylated guanidino derivative. Alternatively, the protected alcohol containing acid can be coupled to produce the acylated guanidino derivative by treatment with a dehydration agent, such as DCC or EDC, with or without a condensation catalyst, such as DMAP. Alternatively the acylating agent may be reacted with the preformed anion of the guanidino functionality prepared by deprotonating the guanidino group with a strong base such as sodium hydride, lithium hexamethyldisilazide or potassium t-butoxide in an inert solvent such as THF. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent, such as thionyl chloride nitrite, thionyl dinitrite or nitrosium tetrafluoroborate, in a suitable anhydrous solvent, such as dichloromethane, THF, DMF or acetonitrile, with or without an amine base, such as pyridine or triethylamine, produces the compounds of structure IIIA.

Figure 6:
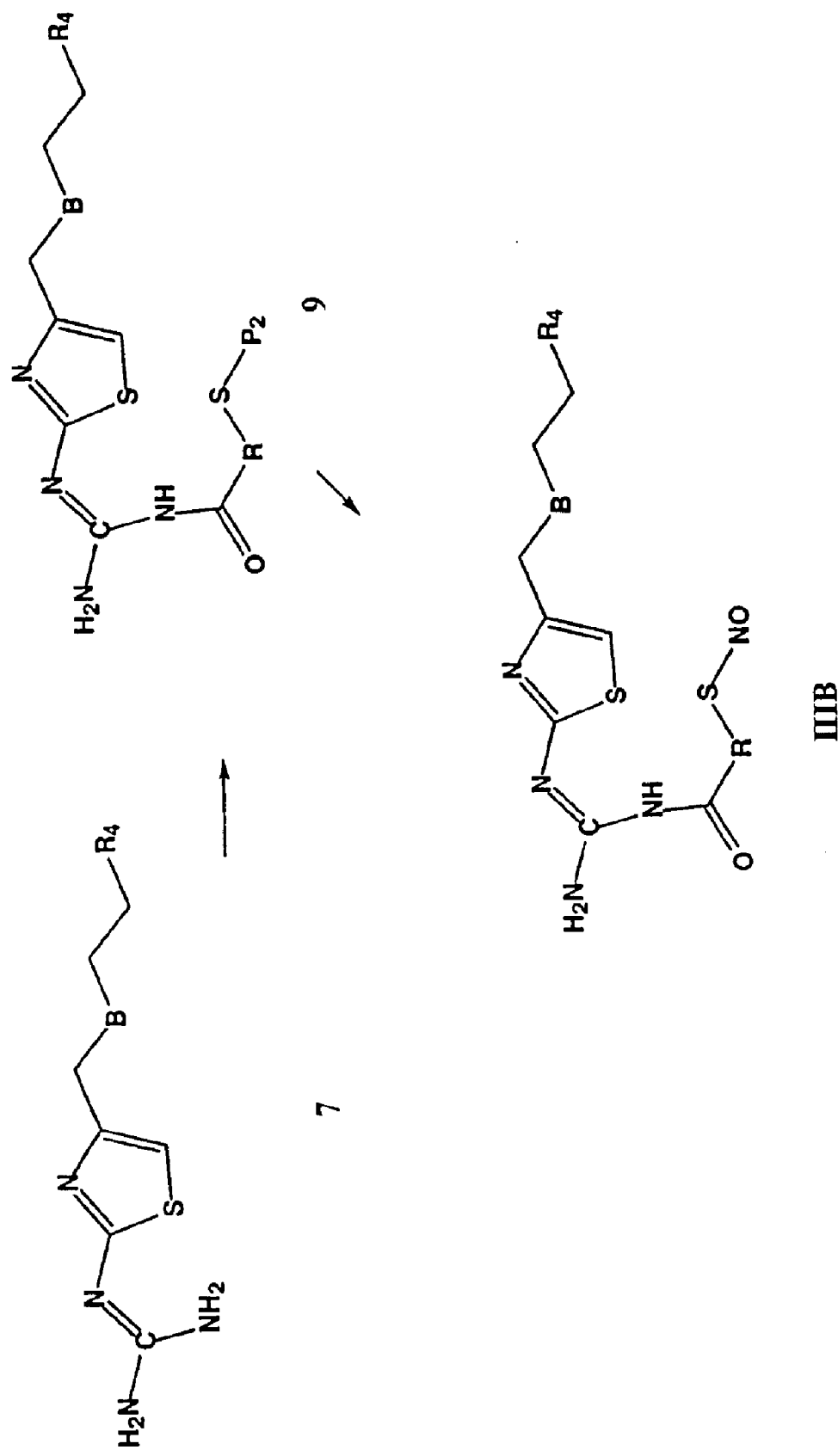
FIG. 6 is the synthetic scheme for the preparation of nitrosothiol-containing guanidino derivatives of the compound of formula (III).

Nitroso compounds of formula (III) wherein B and $R_4$ are as defined herein and a nitrosothiol containing acyl group is representative of the $D_1$ group as defined herein can be prepared as outlined in FIG. 6. The guanidino derivative group of structure 7 is converted to the acylated guanidino derivative of structure 9 by reaction with an appropriate protected thiol containing acid wherein R and $P^2$ are as defined herein. Preferred methods for the preparation of acylated guanidino derivatives are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the guanidino derivative, preferably in the presence of a condensation catalyst, such as DMAP. Alternatively, the acid can first be converted to the acid chloride by treatment with oxalyl chloride in the presence of a catalytic amount of DMF. The acid chloride is then reacted with the guanidino derivative preferably in the presence of a condensation catalyst, such as DMAP, and a tertiary amine base, such as triethylamine, to produce the acylated guanidino derivative. Alternatively, the protected thiol containing acid and guanidino derivative can be coupled to produce the acylated guanidino derivative by treatment with a dehydration agent, such as DCC or EDC with or without a condensation catalyst such as DMAP. Alternatively the acylating agent may be reacted with the preformed anion of the guanidino functionality prepared by deprotonating the guanidino group with a strong base such as sodium hydride, lithium hexamethyldisilazide or potassium t-butoxide in an inert solvent such as THF. Preferred protecting groups for the thiol moiety are as a thioester, such as thioacetate or thiobenzoate, as a disulfide, as a thiocarbamate, such as N-methoxy-methyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenyl-phosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF or acetonitrile, with or without an amine base, such as pyridine or triethylamine, produces the compounds of structure IIIB. Alternatively, a stoichiometric quantity of sodium nitrite in alcoholic or aqueous acid produces the compounds of structure IIIB.

The compounds of the invention include $H_2$ receptor antagonists, such as those described herein, which have been nitrosylated through one or more sites such as oxygen (hydroxyl condensation), sulfur (sulfhydryl condensation), carbon and/or nitrogen. The nitrosated and/or nitrosylated $H_2$ receptor antagonists of the invention are capable of donating, transferring and/or releasing a biologically active form of nitrogen monoxide (i.e., nitric oxide).

Nitrogen monoxide can exist in three forms: NO— (nitroxyl), NO. (uncharged nitric oxide) and $NO^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium ($NO^+$) does not react with $O_2$ or $O_2^-$ species, and functionalities capable of transferring and/or releasing $NO^+$ and NO— are also resistant to decomposition in the presence of many redox metals. Consequently, administration of charged NO equivalents (positive and/or negative) is a more effective means of delivering a biologically active NO to the desired site of action.

Compounds contemplated for use in the invention (e.g., $H_2$ receptor antagonists optionally substituted with one or more NO and/or $NO_2$ groups) are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO.) and charged nitrogen monoxide species, preferably charged nitrogen monoxide species, such as nitrosonium ion ($NO^+$) and nitroxyl ion (NO—). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines (NONOates), (E)-alkyl-2-((E)-hydroxyimino)-5-nitro-3-hexene amines or amides, nitrosoamines, furoxans as well as substrates for the endogenous enzymes which synthesize nitric oxide. The "NO adducts" can be mono-nitrosylated, poly-nitrosylated, mono-nitrosated and/or poly-nitrosated or a combination thereof at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; and (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a carbamoyl, a urea, a nitro, -T-Q, or $(C(R_e)(R_f))_k$-T-Q, or $R_e$ and $R_f$ taken together with the carbon atom to which they are attached are a carbonyl, a methanthial, a heterocyclic ring, a cycloalkyl group or a bridged cycloalkyl group; Q is —NO or —$NO_2$; and T is independently a covalent bond, a carbonyl, an oxygen, —$S(O)_o$— or —$N(R_a)R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—C(T-Q)($R_e$)($R_f$), or —$(N_2O_2-)^-.M^+$, wherein $M^+$ is an organic or inorganic cation; with the proviso that when $R_i$ is —$CH_2$—C(T-Q)($R_e$)($R_f$) or —$(N_2O_2-).M^+$; then "-T-Q" can be a hydrogen, an alkyl group, an alkoxyalkyl group, an aminoalkyl group, a hydroxy group or an aryl group.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof); ON—O, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C-heterocyclic compounds.

Another group of NO adducts for use in the invention include nitrates that donate, transfer or release nitric oxide, such as compounds comprising at least one $O_2N$—O—, $O_2N$—N—, $O_2N$—S— or $O_2N$—C— group. Preferred among these compounds are $O_2N$—O—, $O_2N$—N—, $O_2N$—S— or $O_2N$—C— polypeptides (the term "polypeptide" includes proteins and also polyamino acids that do not possess an ascertained biological function, and derivatives thereof); $O_2N$—O—, $O_2N$—N—, $O_2N$—S— or $O_2N$—C— amino acids (including natural and synthetic amino acids and their stereoisomers and racemic mixtures); $O_2N$—O—, $O_2N$—N—, $O_2N$—S— or $O_2N$—C-sugars; $O_2N$—O—, $O_2N$—C— modified and unmodified oligonucleotides (comprising at least 5 nucleotides, preferably 5–200 nucleotides); $O_2N$—O—, $O_2N$—N—, $O_2N$—S— or $O_2N$—C— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityltetranitrate, mannitol hexanitrate, nitroglycerin, pentaerythritoltetranitrate, pentrinitrol and propatylnitrate.

Another group of NO adducts are N-oxo-N-nitrosoamines that donate, transfer or release nitric oxide and are represented by the formula: $R^1R^2N$—$N(O-M^+)$—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M^+$ is an organic or inorganic cation, such as, for example, an alkyl substituted ammonium cation or a Group I metal cation.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO—) and uncharged nitric oxide (NO.). Compounds where the thiol groups are not sufficiently close to form disulfide bridges generally provide nitric oxide as the NO— form and not as the uncharged NO. form.

The invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine or glutamine, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. USA*, 84:9265–9269 (1987)).

Another aspect of the invention provides methods to decrease or reverse gastrointestinal toxicity and facilitate ulcer healing resulting from the administration of nonsteroidal antiinflammatory drugs (NSAIDs) to a patient. In particular, the invention provides methods of administering a therapeutically effective amount of at least one NSAID with a therapeutically effective amount of the compounds and/or compositions described herein. In one aspect of the invention, the patient can be administered at least one NSAID with a therapeutically effective amount of at least one nitrosated and/or nitrosylated $H_2$ receptor antagonist of the invention to decrease or reverse gastrointestinal toxicity and/or to facilitate ulcer healing resulting from NSAID treatment. In another aspect of the invention, the patient can be administered at least one NSAID with a therapeutically effective amount of at least one nitrosated and/or nitrosylated $H_2$ receptor antagonist of the invention and at least one compound that donates, transfers or releases nitric oxide, or elevates endogenous levels of nitric oxide or EDRF, or is a substrate for nitric oxide synthase, to decrease or reverse gastrointestinal toxicity and/or to facilitate ulcer healing resulting from NSAID treatment. In yet another aspect of the invention, the patient can be administered at least one NSAID with a therapeutically effective amount of at least one $H_2$ receptor antagonist and at least one compound that donates, transfers or releases nitric oxide, or elevates endogenous levels of nitric oxide or EDRF, or is a substrate for nitric oxide synthase, to decrease or reverse gastrointestinal toxicity and/or to facilitate ulcer healing resulting from NSAID treatment. The NSAID, nitrosated and/or nitrosylated $H_2$ receptor antagonist, $H_2$ receptor antagonist, and/or nitric oxide donor can be administered separately or as components of the same composition. These compounds and/or compositions can also be provided in the form of a pharmaceutical kit.

The compounds and compositions of the invention can be used in this aspect of the invention with any NSAID known in the art. Such NSAIDs include, for example, aspirin (e.g., acetylsalicylic acid), salicylate esters and salts, acetate esters of salicylic acid, difluorophenyl derivatives (e.g., diflunisal), salicylsalicylic acids (e.g., salsalate), salts of salicylic acids (e.g., sodium salicylate), salicylamide, sodium thiosalicylate, choline salicylate, magnesium salicylate, combinations of choline and magnesium salicylates, 5-aminosalicylic acid (e.g., mesalamine), salicylazosulfapyridine (e.g., sulfasalazine), methylsalicylate, and the like.

Another group of NSAIDs are the pyrazolon derivatives, which include, for example, phenylbutazone, oxyphenbutazone, antipyrine, aminopyrine, dipyrone and apazone (azapropazone). Another group of NSAIDs are the para-aminophenol derivatives, which are the so-called "coal tar" analgesics, including, for example, phenacetin and its active metabolite acetaminophen. Another group of compounds include indomethacin, a methylated indole derivative, and the structurally related compound sulindac.

Yet another group of compounds is the fenamates which are derivatives of N-phenylanthranilic acid (e.g., mefenamic, meclofenamic, flufenamic, tolfenamic and etofenamic acids). Another contemplated NSAID is tolmetin.

Another group of NSAIDs are the propionic acid derivatives. Principal members of this group are, for example, ibuprofen, naproxen, flurbiprofen, fenoprofen and ketoprofen. Other members of this group include, for example, fenbufen, pirprofen, oxaprozin, indoprofen and tiaprofenic acid.

Still other NSAIDs are piroxicam, ampiroxicam, oxicam derivatives (which are a class of antinflammatory enolic acids), tenoxicam tenidap, diclofenac (one of the series of phenylacetic acid derivatives that have been developed as antiinflammatory agents). Other NSAIDs include etodolac and nabumentone.

Each of the above contemplated NSAIDs is described more fully in the literature, such as in Goodman and Gilman, The Pharmacological Basis of Therapeutics (9th Edition), McGraw-Hill, 1995, Pgs. 617–657; the Merck Index on CD-ROM, Twelfth Edition, Version 12:1, 1996.

Other NSAIDs that can be used in the invention include those described in U.S. Pat. No. 5,703,073, the disclosure of which is incorporated by reference herein in its entirety.

Another aspect of the invention provides methods to improve the gastroprotective properties, anti-*Helicobacter* properties and antacid properties of $H_2$ receptor antagonists by administering to a patient in need thereof a therapeutically effective amount of the compounds and/or compositions described herein. In one aspect of the invention, the patient can be administered at least one nitrosated and/or nitrosylated $H_2$ receptor antagonist of the invention to improve the gastroprotective properties, anti-*Helicobacter* properties and antacid properties of the $H_2$ receptor antagonist. In another aspect of the invention, the patient can be administered a bismuth-complex comprising at least one nitrosated and/or nitrosylated $H_2$ receptor antagonist of the invention to improve the gastroprotective properties, anti-*Helicobacter* properties and antacid properties of the $H_2$ receptor antagonist. In another aspect of the invention, the patient can be administered at least one nitrosated and/or nitrosylated $H_2$ receptor antagonist of the invention and at least one compound that donates, transfers or releases nitric oxide, or elevates endogenous levels of nitric oxide or EDRF, or is a substrate for nitric oxide synthase, to improve the gastroprotective properties, anti-*Helicobacter* properties and antacid properties of the $H_2$ receptor antagonist. In another aspect of the invention, the patient can be administered a bismuth complex comprising at least one nitrosated and/or nitrosylated $H_2$ receptor antagonist of the invention and at least one compound that donates, transfers or releases nitric oxide, or elevates endogenous levels of nitric oxide or EDRF, or is a substrate for nitric oxide synthase, to improve the gastroprotective properties, anti-*Helicobacter* properties and antacid properties of the $H_2$ receptor antagonist. In yet another aspect of the invention, the patient can be administered at least one $H_2$ receptor antagonist and at least one compound that donates, transfers or releases nitric oxide, or elevates endogenous levels of nitric oxide or EDRF, or is a substrate for nitric oxide synthase, to improve the gastroprotective properties, anti-*Helicobacter* properties and antacid properties of the $H_2$ receptor antagonist. In yet another aspect of the invention, the patient can be administered a bismuth-complex comprising at least one $H_2$ receptor antagonist and at least one compound that donates, transfers or releases nitric oxide, or elevates endogenous levels of nitric oxide or EDRF, or is a substrate for nitric oxide synthase, to improve the gastroprotective properties, anti-*Helicobacter* properties and antacid properties of the $H_2$ receptor antagonist.

The bismuth-containing reagent, $H_2$ receptor antagonist, that is optionally, substituted with at least one NO and/or $NO_2$ group, and nitric oxide donor can be administered separately or as components of the same composition. The $H_2$ receptor antagonists, optionally substituted with at least one NO and/or $NO_2$ group, and nitric oxide donors are described in detail herein. Bismuth complexes are prepared by boiling the aqueous solution of the free base of the $H_2$ receptor antagonist with at least one bismuth containing reagent, including, for example, bismuth citrate, bismuth salicylate, bismuth tartaric acid or mixtures thereof.

Another aspect the invention provides methods for preventing or treating gastrointestinal disorders by administering to the patient in need thereof a therapeutically effective amount of the compounds and/or compositions described herein. Such gastrointestinal disorders include, for example, peptic ulcers, stress ulcers, gastric hyperacidity, dyspepsia, gastroparesis, Zollinger-Ellison syndrome, gastroesophageal reflux disease, short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. In one aspect of the invention, the patient can be administered at least one nitrosated and/or nitrosylated $H_2$ receptor antagonist of the invention to prevent or treat the gastrointestinal disorder. In another aspect of the invention, the patient can be administered at least one antacid and at least one nitrosated and/or nitrosylated $H_2$ receptor antagonist of the invention to prevent or treat the gastrointestinal disorder. In another aspect of the invention, the patient can be administered at least one nitrosated and/or nitrosylated $H_2$ receptor antagonist of the invention and at least one compound that donates, transfers or releases nitric oxide, or elevates endogenous levels of nitric oxide or EDRF, or is a substrate for nitric oxide synthase, to prevent or treat the gastrointestinal disorder. In still another aspect of the invention, the patient can be administered at least one antacid, at least one nitrosated and/or nitrosylated $H_2$ receptor antagonist of the invention, and at least one compound that donates, transfers or releases nitric oxide, or elevates endogenous levels of nitric oxide or EDRF, or is a substrate for nitric oxide synthase, to prevent or treat the gastrointestinal disorder. In yet another aspect of the invention, the patient can be administered at least one $H_2$ receptor antagonist and at least one compound that donates, transfers or releases nitric oxide, or elevates endogenous levels of nitric oxide or EDRF, or is a substrate for nitric oxide synthase, to prevent or treat the gastrointestinal disorder. In yet another aspect of the invention, the patient can be administered at least one antacid, at least one $H_2$ receptor antagonist, and at least one compound that donates, transfers or releases nitric oxide, or elevates endogenous levels of nitric oxide or EDRF, or is a substrate for nitric oxide synthase, to prevent or treat the gastrointestinal disorder.

The antacid, $H_2$ antagonist that is optionally substituted with at least one NO and/or $NO_2$ group, and the nitric oxide donor can be administered separately or as components of the same composition. These compounds and/or compositions can also be provided in the form of a pharmaceutical kit. The $H_2$ receptor antagonists substituted with at least one NO and/or $NO_2$ group and preferred nitric oxide donors are described in detail herein. Appropriate antacids for use in this aspect of the invention include any antacids known in the art, including, for example, aluminum hydroxide, magnesium hydroxide, magnesium carbonate, calcium carbonate and co-dried gels, such as, for example, aluminum hydroxide-magnesium carbonate co-dried gel.

Another aspect of the invention provides methods for preventing and treating inflammations and/or microbial infections by administering the compounds and/or compositions described herein. The inflammations and/or microbial infections that are being prevented or treated are preferably those of the eyes, ears, nose or skin. In one aspect of the invention, the patient can be administered at least one nitrosated and/or nitrosylated $H_2$ receptor antagonist of the invention to treat the inflammation or microbial infection. In another aspect of the invention, the patient can be administered at least one nitrosated and/or nitrosylated $H_2$ receptor antagonist of the invention and at least one compound that donates, transfers or releases nitric oxide, or elevates endogenous levels of nitric oxide or EDRF, or is a substrate for nitric oxide synthase, to treat the inflammation or microbial infection. In yet another aspect of the invention, the patient can be administered at least one $H_2$ receptor antagonist and at least one compound that donates, transfers or releases nitric oxide, or elevates endogenous levels of nitric oxide or EDRF, or is a substrate for nitric oxide synthase, to treat the inflammation or microbial infection. The $H_2$ receptor antagonist that is optionally substituted with at least one NO and/or $NO_2$ group and the nitric oxide donor can be administered separately or as components of the same composition.

Another aspect of the invention provides methods for preventing and treating ophthalmic diseases and disorders by administering the compounds and/or compositions described herein. The ophthalmic diseases and disorders include glaucoma, inflammation of the eye and elevation of intraocular pressure. In one aspect of the invention, the patient can be administered at least one nitrosated and/or nitrosylated $H_2$ receptor antagonist of the invention to treat the ophthalmic diseases and disorders. In another aspect of the invention, the patient can be administered at least one nitrosated and/or nitrosylated $H_2$ receptor antagonist of the invention and at least one compound that donates, transfers or releases nitric oxide, or elevates endogenous levels of nitric oxide or EDRF, or is a substrate for nitric oxide synthase, to treat the ophthalmic diseases and disorders. In yet another aspect of the invention, the patient can be administered at least one $H_2$ receptor antagonist and at least one compound that donates, transfers or releases nitric oxide, or elevates endogenous levels of nitric oxide or EDRF, or is a substrate for nitric oxide synthase, to treat the ophthalmic diseases and disorders. The $H_2$ receptor antagonist that is optionally substituted with at least one NO and/or $NO_2$ group and the nitric oxide donor can be administered separately or as components of the same composition.

Another aspect the invention provides methods for treating multiple sclerosis, and viral infections, such as HIV disease, by administering to the patient a therapeutically effective amount of the compounds and/or compositions described herein. In one aspect of the invention, the patient can be administered at least one nitrosated and/or nitrosylated $H_2$ receptor antagonist of the invention to treat multiple sclerosis or the viral infection. Treating a viral infection can further comprise administering at least one anti-viral agent to the patient. In another aspect of the invention, the patient can be administered at least one nitrosated and/or nitrosylated $H_2$ receptor antagonist of the invention, at least one compound that donates, transfers or releases nitric oxide, or elevates endogenous levels of nitric oxide or EDRF, or is a substrate for nitric oxide synthase, to treat multiple sclerosis or the viral infection. Treating a viral infection can further comprise administering at least one anti-viral agent to the patient. In yet another aspect of the invention, the patient can be administered at least one $H_2$ receptor antagonist and at least one compound that donates, transfers or releases nitric oxide, or elevates endogenous levels of nitric oxide or EDRF, or is a substrate for nitric oxide synthase, to treat multiple sclerosis or the viral infection. Treating a viral infection can further comprise administering at least one anti-viral agent to the patient.

The $H_2$ receptor antagonist that is substituted with at least one NO and/or $NO_2$ group, the anti-viral agents, and the nitric oxide donor can be administered separately or as components of the same composition. The $H_2$ receptor antagonists substituted with at least one NO and/or $NO_2$ group and preferred nitric oxide donors are described in detail above. Appropriate anti-viral agents include any anti-viral agent known in the art, including, for example, metronidazole, AZT (3'-azidothymidine), DDI (2',3'-dideoxyinosine), DDC (2',3'-dideoxycytidine), L-735,524 (N-(2-(R)-hydroxy-1(S)-indanyl)-2(R)-phenylmethyl-4-(S)-hydroxy-5-(1-(4-(3-pyridylmethyl)-2(S)-N'-(butylcarboxamido)-piperazinyl))-pentaneamide), and the like. These compounds and/or compositions can also be provided in the form of a pharmaceutical kit. Preferred $H_2$ receptor antagonists, including those that are substituted with at least one NO and/or $NO_2$ group, and preferred nitric oxide donors are described in detail herein.

When administered in vivo, the compounds and compositions of the invention can be administered in combination with pharmaceutically acceptable carriers and in dosages described herein. While the compounds and compositions of the invention can be administered as a mixture of an $H_2$ receptor antagonist that is optionally substituted with at least one NO and/or $NO_2$ group and a nitric oxide donor, they can also be used in combination with one or more additional compounds (e.g., NSAIDs, antacids, bismuth-containing reagents, anti-viral agents) which are known to be effective against the specific disease state that one is targeting for treatment. The nitric oxide donor(s) can be administered simultaneously with, subsequently to, or prior to administration of the $H_2$ receptor antagonist that is optionally substituted with at least one NO and/or $NO_2$ group, and/or other additional compounds.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional non-toxic pharmaceutically acceptable carriers, adjuvants, and vehicles, as desired. Parenteral includes subcutaneous injections, intravenous, intramuscular, intrastemal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like.

The bioavailability of the compositions can be enhanced by micronization of the formulations using conventional techniques such as grinding, milling, spray drying and the like in the presence of suitable excipients or agents such as phospholipids or surfactants.

The compounds and compositions of the invention can be formulated as neutral or pharmaceutically acceptable salt forms. Pharmaceutically acceptable salts include, for example, those formed with free amino groups such as those derived from hydrochloric, hydrobromic, phosphoric, sulfuric, acetic, citric, benzoic, fumaric, glutamic, lactic, malic, maleic, nitric, succinic, tartaric p-toluene-sulfonic, methanesulfonic, acids, gluconic acid, and the like, and those formed with free carboxyl groups such as those derived from sodium, potassium, ammonium, calcium, ferric hydroxides, isopropylamine, triethylamine, 2-ethylamino ethanol, histidine, procaine, and the like.

"Therapeutically effective amount" refers to the amount of the $H_2$ receptor antagonist, that is optionally substituted with at least one NO and/or $NO_2$ group, and nitric oxide donor that is effective to achieve its intended purpose. While individual patient needs may vary, determination of optimal ranges for effective amounts of each of the compounds and compositions is within the skill of the art. Generally, the dosage required to provide an effective amount of the composition, and which can be adjusted by one of ordinary skill in the art will vary, depending on the age, health, physical condition, sex, weight, extent of the dysfunction of the recipient, frequency of treatment and the nature and scope of the dysfunction or disease.

The amount of a given $H_2$ receptor antagonist, that is optionally substituted with at least one NO and/or $NO_2$ group, which will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the $H_2$ receptor antagonist. The usual daily doses of $H_2$ receptor antagonists are about 1 mg to about 10 g per day and the doses of nitric oxide donors in the pharmaceutical composition can be in amounts of about 0.001 mg to about 40 g, while that actual amount will be dependent upon the specific nitric oxide donor. Effective doses may be extrapolated from dose-response curves derived from in vitro or animal model test systems and are in the same ranges or less than as described for the commercially available compounds in the Physician's Desk Reference, supra.

The invention also provides pharmaceutical kits comprising one or more containers filled with one or more of the ingredients of the pharmaceutical compounds and/or compositions of the invention, including, at least, one or more of the $H_2$ receptor antagonists, that are optionally substituted with at least one NO and/or $NO_2$ group, described herein and one or more of the NO donors described herein. Associated with such kits can be additional compounds or compositions (e.g., NSAIDs, antacids, bismuth-containing reagents, antiviral agents, permeation enhancers, lubricants, and the like), devices for administering the compositions, and notices in the form prescribed by a governmental agency regulating the manufacture, use or sale of pharmaceuticals or biological products which reflects approval by the agency of manufacture, use or sale for humans.

EXAMPLES

The following non-limiting examples further describe and enable one of ordinary skill in the art to make and use the invention. In each of the examples, flash chromatography was performed on 40 micron silica gel (Baker).

Example 1

(2Z)-2-aza-3-(methylamino)-3-((2-((5-methyl-1-(2-(2-(nitrosothio)adamantan-2-yl)acetyl)imidazol-4-yl)methylthio)ethyl)amino)prop-2-enenitrile 1a. Adamantane-2-thione Adamantan-2-one (48.46 g, 322.6 mmol) in pyridine (300 mL) was heated to 90° C., and phosphorous pentasulfide (17.84 g, 40.13 mmol) was added. The reaction was maintained at 90° C. for two hours, and at room temperature overnight, during which time a precipitate formed. The pyridine solution was decanted and concentrated to dryness. The residual semisolid was treated with hexane (400 mL) to give an orange solution with a light brown suspension. The suspension was removed by filtration. The filtrate was concentrated to dryness and dried under vacuum to give an orange solid (50.36 g). This crude product was purified by filtration through a pad of silica gel (hexane). $^1$H NMR (300 MHz, $CDCl_3$): δ 3.43 (s, 2H), 2.1–1.9 (m, 12H). $^{13}$C NMR (75 MHz, $CDCl_3$): δ 222.4, 57.5, 41.1, 36.5, 27.4.

1b. Tert-butyl 2-(2-sulfanyladamantan-2-yl)acetate

To t-butyl acetate (25 mL, 21.6 g, 186 mmol) in dry THF (400 mL) at −78° C. was added lithium diisopropylamide monotetrahydrofuran (1.5 M solution in cyclohexane, 100 mL, 150 mmol) under nitrogen. It was stirred at −78° C. for 40 minutes. The product of Example 1a (21.88 g, 131.57 mmol) in THF (400 mL) was added. The cold bath was removed and the reaction was stirred at room temperature for two hours. The reaction was diluted with methylene chloride, and 2 M HCl (75 mL) was added. The organic phase was separated, washed with brine (4×40 mL), dried ($MgSO_4$), filtered, and concentrated. The crude product was purified by filtration through a pad of silica gel (5% EtOAc/95% hexane) to give the title compound (34.67 g, 122.7 mmol, 93%). $R_f$=0.48 (EtOAc/hexane 1:19). $^1$H NMR (300 MHz, $CDCl_3$): δ 2.87 (s, 2H), 2,47 (d, J=11.5, 2H), 2.38 (s, 1H), 2.11 (d, J=11.9, 2H), 1.98 (s, 2H), 1.96 (m, 2H), 1.84–1.62 96 (m, 6H), 1.47 (s, 9H). $^{13}$C NMR (75 MHz, $CDCl_3$): δ 170.8, 80.7, 54.1, 47.3, 39.0, 38.2, 37.2, 36.6, 34.0, 33.3, 28.2, 27.5, 26.9. APIMS (IS, $NH_4OAc$) m/e 283 ($MH^+$). Anal. Calcd. for $C_{16}H_{26}O_2S$ (282.44): C, 68.04; H, 9.28. Found: C, 68.14; H, 9.30.

1c. 2-(2-sulfanyladamantan-2-yl)acetic acid

To the product of Example 1b (10.76 g, 38.1 mmol) in methylene chloride (15 ml) was added trifluoroacetic acid (TFA) (15 mL). The reaction was stirred at room temperature for 40 minutes and concentrated to dryness. The residue was treated with methylene chloride and concentrated to dryness three times. The residual solid was triturated with methylene chloride (20 ml). Solid was collected by filtration, washed with a small amount of methylene chloride, and dried in vacuum to give the title compound (5.6447 g, 24.94 mmol, 65%). $^1$H NMR (300 MHz, $CDCl_3$): δ 9.5 (broad, 1H), 3.04 (s, 2H), 2.49 (d, J=11.2, 2H), 2.25 (s, 1H), 2.1–2.0 (m, 4H), 1.9 (m, 2H), 1.7–1.6 (m, 6H). $^{13}$C NMR (75 MHz, $CDCl_3$): δ 177.7, 53.4, 46.3, 38.9, 37.8, 33.8, 33.2, 27.4, 26.8. APIMS (IS, $NH_4OAc$) m/e 225 ($M-H^+$). Anal. Calcd for $C_{12}H_{18}O_2S$ (226.33): C, 63.68; H, 8.02. Found: C, 63.40; H, 7.90.

1d. 2-(2-(Nitrosothio)adamantan-2-yl)acetic acid

The product of Example 1c (773.1 mg, 3.416 mmol) was dissolved in hot methylene chloride (40 mL). The methylene chloride solution was cooled to room temperature and t-butyl nitrite (420 mL, 370 mg, 3.59 mmol) was added. The reaction immediately turned green and was stirred at room temperature for 30 minutes. Some methylene chloride (15 mL) was evaporated at reduced pressure to give a suspension. This suspension was stored in refrigerator over the weekend and purified by column chromatography (silica gel, 25% EtOAc/75% hexane) to give the title compound (628.2 mg, 2.46 mmol, 72%). $^1$H NMR (300 MHz, $CDCl_3$): δ 10.8 (broad, 1H), 3.77 (s, 2H), 2.78 (s, 2H), 2.4 (m, 2H), 2.1–1.7 (m, 10H). $^{13}$C NMR (75 MHz, $CDCl_3$): δ 177.0, 65.2, 42.1 38.8, 35.4, 33.7, 33.1, 27.1. APIMS (IS, $NH_4OAc$) m/e 254 (M−H_).

1e. (2Z)-2-aza-3-(methylamino)-3-((2-((5-methyl-1-(2-(2-(nitrosothio)-adamantan-2yl)acetyl)imidazol-4-yl)methylthio)amino)prop-2-enenitrile To an ice-cooled suspension of the product of Example 1d (2.16 g, 8.46 mmol) and (2Z)-2-aza-3-(methylamino)-3-((2-((5-methylimidazol-4-yl)methylthio)ethyl) amino)prop-2-enenitrile (2.34 g, 9.27 mmol) in dichloromethane (90 mL) was added a solution of 1 M 1,3-dicyclohexylcarbodiimide (DCC) in dichloromethane (10.7 ml, 10.7 mmol). After 30 minutes, the reaction was warmed to room temperature and stirred for 1 hour. To the reaction was added water (100 ml). After separation of layers, the aqueous layer was extracted by dichloromethane (2×50 ml). The combined organic layers were dried with sodium sulfate and evaporated to dryness. The residue was purified by flash chromatography (SiO$_2$, ethyl acetate followed by 3–5% methanol/ethyl acetate). The title compound was obtained as a green foam (1.10 g, 26.5%). Rf=0.58 (SiO$_2$, 10% methanol in ethyl acetate); $^1$H NMR (300 MHz, CDCl$_3$): δ 1.79–2.12 (m, 10H), 2.33 (s, 3H), 2.47 (d, J=13.1 Hz, 2H), 2.68 (t, J=6.4 Hz, 2H), 2.85 (d, J=4.0 Hz, 3H), 2.96 (s, 2H), 3.43 (d, J=5.7 Hz, 2H), 3.59 (s, 2H), 4.40 s, 2H), 6.59 (s, 1H), 6.74 (br s, 1H), 7.96 (s, 1H); $^{13}$C NMR (75 MHz, CDCl$_3$): δ 11.08, 2.63, 26.67, 28.05, 32.88, 33.28, 35.37, 38.29, 40.91, 42.77, 66.00, 118.86, 125.03, 135.49, 137.06, 160.16, 167.95; LCMS (m/e): 490 (M$^+$).

Example 2

(N-(3-(3-(piperidylmethyl)phenoxy)propyl) carbamoyl)methyl 2-(2-(nitrosothio)adamantan-2-yl) acetate To an ice-cooled solution of the product of Example 1d (0.589 g, 2.31 mmol), 2-hydroxy-N-(3-(3-(piperdylmethyl) phenoxy)propyl)acetamide (0.706 g, 2.30 mmol) and DMAP (10 mg) in dichloromethane (20 mL) was added a solution of 1 M DCC in dichloromethane (2.5 mL, 2.5 mmol). After 30 minutes, the reaction was warmed to room temperature and stirred for 1 hour. The reaction was diluted with dichloromethane (30 mL) and washed with water (30 mL). After drying over sodium sulfate and concentration under vacuum, the residue was purified by flash chromatography (SiO$_2$, 10% methanol in ethyl acetate) to afford the title compound as a green oil (0.45 g, 35.9%). $^1$H NMR (300 MHz, CDCl$_3$): δ 1.30–1.35 (m, 2H), 1.55–1.60 (m, 4H), 1.74–2.03 (m, 12H), 2.34–2.40 (m, 6H), 2.75 (br s, 2H), 3.44–3.55 (m, 2H), 3.46 (s, 2H), 3.82 (s, 2H), 4.03 (t, J=5.9 Hz, H), 4.44 (s, 2H), 6.39 (br t, J=5.0 Hz, 1H), 6.79 (d, J=7.5 1H), 6.90 (d, J=7.0 Hz, 1H), 6.92 (s, 1H), 7.20 (t, J=7.9 Hz, 1H); $^{13}$C NMR (75 MHz, CDCl$_3$): δ 24.03, 25.52, 26.79, 28.61, 32.88, 33.48, 35.34, 36.69, 38.48, 41.83, 54.11, 62.57, 63.34, 65.71, 112.98, 115.07, 121.73, 128.86, 139.64, 158.45, 166.67, 168.77; MS (m/e): 544 (M+).

Example 3

(N-3(-(3-(piperidylmethyl)phenoxy)propyl) carbamoyl)methyl 3-(N-(2-methyl-2-(nitrosothio) propyl)carbamoyl)propanoate 3a. 3-(N-(2-methyl-2-sulfanylpropyl)carbamoyl)propanoic acid To an ice-cooled suspension of 1-amino-2-methylpropan2-thiol hydrochloride (5.06 g, 35.72 mmol) in methylene chloride (100 mL) was added triethylamine (5.0 mL, 35.87 mmol) followed by succinic anhydride (3.50 g, 34.96 mmol). The resulting clear solution was stirred at 0° C. or 10 minutes, then at room temperature for 2 hours. Evaporation of the volatiles under reduced pressure gave a residue which was partitioned between 2 N hydrochloric acid (100 mL) and ethyl acetate (100 mL). The aqueous layer was extracted with ethyl acetate (3×100 mL). The combined organic layers were washed with brine (5 mL), dried over sodium sulfate and evaporated to dryness. The residue was triturated with ether-hexane to afford the title compound as a white solid (6.78 g, 94.4%). Mp. 86–87° C.; $^1$H NMR (300 MHz, CDCl$_3$): δ 1.34 (s, 6H), 1.55 (s, 1H), 2.59 (t, J=6.6 Hz, H), 2.70 (t, J=6.6 Hz, 2H), 3.32 (d, J=8.0 Hz, 2H), 6.58 (br t, J=5.9 Hz, 1H), 10.73 (br s, 1H); $^{13}$C NMR (75 MHz, CDCl$_3$): δ 29.57, 29.79, 30.79, 172.50, 176.81; LCMS (m/e): 223 (M+H$_2$O), 206 (M+1).

3b. (N-3 (-(3-(piperidylmethyl)phenoxy)propyl)carbamoyl) methyl 3-(N-(2-methyl-2 sulfanylpropyl)carbamoyl) propanoate To an ice-cooled solution of 2-hydroxy-N-(3-(3-(piperdylmethyl)phenoxy)propyl)acetamide (1.12 g, 3.66 mmol), the product of Example 3a (0.83 g, 4.04 mmol) and DMAP (30 mg) in dichloromethane (50 mL) was added a solution of 1 M DCC in dichloromethane (4.75 mL, 4.75 mmol). The reaction was stirred at 0° C. for 30 minutes and at room temperature for 2 hours. Additional 2-hydroxy-N-(3-(3-(piperdyl-methyl)phenoxy)propyl)acetamide (0.39 g) and 1 M DCC in dichloromethane (2 mL) was added and stirring was continued for 1 hour. The reaction was washed with water (50 mL) and the aqueous phase was extracted with dichloromethane (2×50 mL). The combined organic phase was dried (Na$_2$SO$_4$) and concentrated under reduced pressure. The crude product was purified by flash chromatography (SiO$_2$, ethyl acetate, then 10% methanol/ethyl acetate, followed by 1:10:90 triethylamine/methanol/ethyl acetate) to afford the title compound as a viscous oil (1.099 g, 60.9%). $^1$H NMR (300 Hz, CDCl$_3$): δ 1.31 (s, 6H), 1.33 (s, 1H), 1.41–1.44 (m, 2H), 1.53–1.67 (m, 4H), 2.01–2.07 (m, 2H), 2.37 (m, 4H), 2.63 (m, 4H), 3.27 (d, J=6.2 Hz, 2H), 3.39 (s, 2H), 3.47 (q, J=6.0 Hz, 2H), 4.01 (t, J=6.1 Hz, 2H), 4.63 (s, 2H), 6.39 (br t, J=5.8 Hz, 1H), 6.76 (dd, J=7.5 and 1.9 Hz, 1H), 6.87 (s, 1H), 6.89 (d, J=6.6 Hz, 1H), 7.19 (t, J=7.9 Hz, 1H), 7.50 (br t, J=5.2 Hz, 1H); $^{13}$C NMR (75 MHz, CDCl$_3$): δ 24.21, 25.81, 28.78, 29.47, 29.82, 30.78, 36.59, 45.09, 52.20, 54.35, 62.73, 63.63, 65.54, 112.73, 115.16, 121.53, 128.89, 140.14, 158.64, 167.52, 171.69, 171.80; MS (m/e): 494 (M$^+$).

3c. (N-3(-(3-(piperidylmethyl)phenoxy)propyl)carbamoyl) methyl 3-(N-(2-methyl-2-(nitrosothio)propyl)carbamoyl) propanoate To a solution of the product of Example 3b (0.486 g, 0.98 mmol) in dichloromethane (10 mL) was added a saturated solution of HCl in methanol (2 mL). Tert-butyl nitrite (0.127 mL, 1.08 mmol) was introduced to the reaction which immediately turned greenish. After 30 minutes, the reaction was evaporated under vacuum. The residue was partitioned between aqueous saturated potassium bicarbonate (30 mL) and dichloromethane (30 mL). After separation, the aqueous layer was extracted with dichloromethane (2×20 mL). The combined organic layers were dried (Na$_2$SO$_4$) and concentrated under vacuum to afford the crude product which was purified by flash chromatography (SiO$_2$, ethyl acetate, then 10% methanol/ethyl acetate, then 1:10:90 triethylamine/methanol/ethyl acetate). The title compound (0.421 g, 81.8%) was isolated as a green oil. $^1$H NMR (300 MHz, CDCl$_3$): δ 1.34–1.43 (m, 2H), 1.54–1.57 (m, 4H), 1.82 (s, 6H), 2.04–2.07 (m, 2H), 2.36 (m, 4H), 2.61 (m, 4H), 3.43 (s, 2H), 3.47 (q, J=5.9 Hz, 2H), 3.96 (d, J=6.5 Hz, 2H), 4.02 (t, J=6.0 Hz, 2H), 4.60 (s, 2H), 6.65 (br t, J=5.6 Hz, 1H), 6.76 (d, J=7.7 Hz, 1H), 6.87 (s, 1H), 6.88 (d, J=6.3 Hz, 1H), 7.19 (t, J=8.0 Hz, 1H), 7.52 (br t, J=5.2 Hz, 1H); $^{13}$C NMR (75 MHz, CDCl$_3$): δ 24.16, 25.74, 26.62, 28.75, 29.42, 30.65, 36.61, 49.32, 54.33, 56.94, 62.66, 63.60, 65.50, 112.76, 115.18, 121.58, 128.90, 139.99, 158.63, 167.54, 171.78, 172.12; MS (m/e): 523 (M$^+$).

Example 4

Comparative In Vivo Gastric Lesion Activity

The ethanol/HCl mixture-induced gastric lesion test in rats described by Takeuchi et al, *J. Pharmacol. Exp. Ther.,* 286: 115–121 (1998), was used to evaluate the gastric lesion activity. Male Sprague Dawley rats (Charles River Laboratories, Wilmington, Mass.) weighing 230–250 g were used for the experiments. The rats were housed with laboratory chow and water ad libitum prior to the study. The rats were fasted for 24 hours with free access to water and then dosed by oral gavage with vehicle or with the test compounds given at a volume of 0.5 ml/100 g body weight. Thirty minutes after oral dosing all the rats received 1 ml of a solution of 60% ethanol in 150 mM HCl intragastrically. Food was withheld after dosing. Sixty minutes after ethanol/HCl, rats were euthanized by pre-charged $CO_2$. The stomachs were dissected along the greater curvature, washed with a directed stream of 0.9% saline and pinned open on a sylgard based petri dish for examination of the hemorrhagic lesions. Gastric lesion score was expressed in mm and calculated by summing the length of each lesion as described by Al-Ghamdi et al, *J. Int. Med. Res.*, 19: 2242 (1991). Results are expressed as the mean±standard error of the mean. Statistical analysis were conducted using ANOVA test followed by a Student-Newman-Keuls post-hoc test using the Abacus Concepts, Super Anova computer program (Abacus Concepts, Inc., Berkeley, Calif.).

Figure 7:
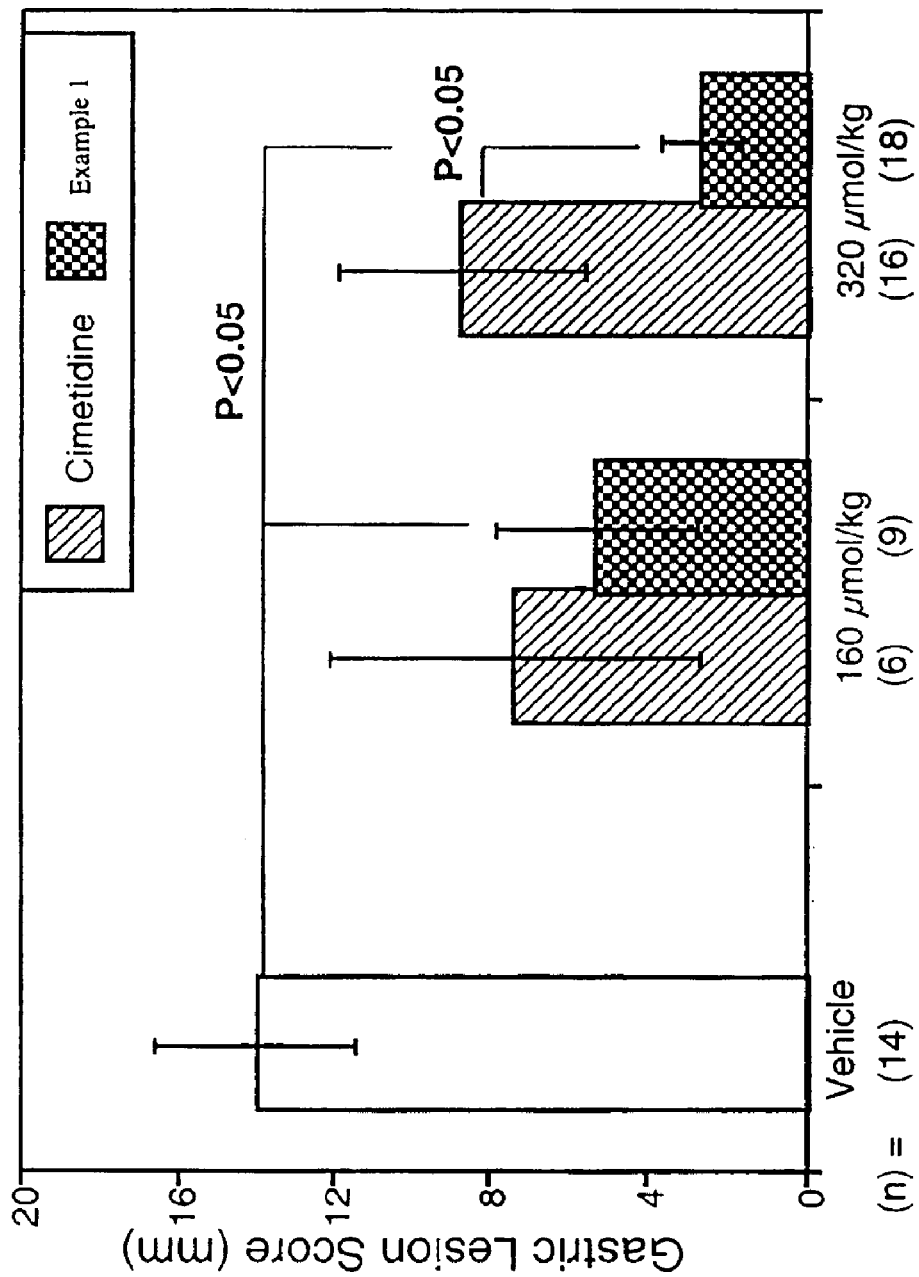
FIG. 7 shows the gastric lesion scores of (a) vehicle alone (open bar, n=14); (b) cimetidine in vehicle (stripped bar); and (c) example 1 (nitrosylated cimetidine) in vehicle (checked bar). Cimetidine at 160 $\mu$mol/kg (n=6) and 320 $\mu$mol/kg (n=16) did not significantly inhibit the formation of gastric lesions relative to vehicle alone. Example 1 (nitrosylated cimetidine) at 160 $\mu$mol/kg (n=9) and 320 $\mu$mol/kg (n=18) inhibited the formation of gastric lesions relative to vehicle alone ($p<0.05$). At the higher concentration, the gastric lesion score of example 1 and cimetidine were significantly different ($p<0.05$).

FIG. 7 compares the gastric lesion activity of vehicle alone, cimetidine in vehicle and Example 1 (nitrosylated cimetidine) in vehicle. Ethanol/HCl mixture produced gastric lesion in the control rats treated with vehicle (0.5% Methocel). Cimetidine at doses of 160 and 320 μmol/kg failed to significantly inhibit the formation of gastric lesions. However, Example 1, the nitrosylated cimetidine derivative, at 160 and 320 μmol/kg significantly inhibited the formation of gastric lesions produced by the ethanol/HCl mixture.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A compound of Formula (I), or a pharmaceutically acceptable salt thereof, wherein the compound of Formula (I) is:

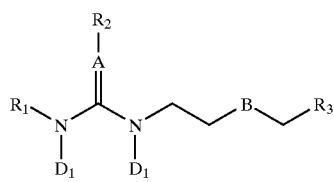

(I)

wherein

A is CH, nitrogen or sulfur;

B is oxygen, $S(O)_o$ or $CH_2$;

o is an integer from 0 to 2;

$D_1$ is a hydrogen atom or D;

$R_1$ is a hydrogen atom, a lower alkyl group, a cycloalkylalkyl group, a hydroxyalkyl group, an alkoxyalkyl group or an aminoalkyl group;

$R_2$ is a lone pair of electrons, a nitrile group, a nitro group, an alkylsulfonyl group, an arylsulfonyl group, an alkylcarbonyl group, a carboxamido group, a carboxylic ester or a cycloalkylalkyl group;

$R_3$ is:

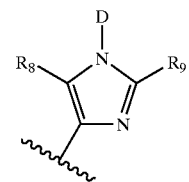

(1)

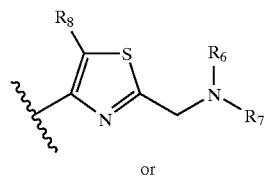

(2)

or

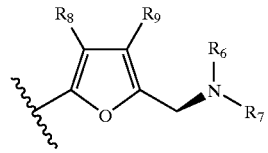

(3)

with the proviso that at least one $D_1$ must be D if there is no D designated in the structure;

$R_6$ and $R_7$ are each independently K, a hydrogen atom, a lower alkyl group, an alkylaryl group, an arylcarbonyl group, an alkylcarbonyl group, or $R_6$ and $R_7$ taken together with the nitrogen atom to which they are attached are a heterocyclic ring;

$R_8$ and $R_9$ are independently a hydrogen atom or a lower alkyl group;

D is Q or K; with the proviso that D cannot be —NO or —$NO_2$;

Q is —NO or —$NO_2$;

K is -$W_a$-$E_b$-$(C(R_e)(R_f))_p$-$E_c$-$(C(R_e)(R_f))_x$-$W_d$-$(C(R_e)(R_f))_y$-$W_i$-$E_j$-$W_g$-$(C(R_e)(R_f))_z$-T-Q;

a, b, c, d, g, i and j are each independently an integer from 0 to 3;

p, x, y and z are each independently an integer from 0 to 10;

W at each occurrence is independently —C(O)—, —C(S)—, -T-, —$(C(R_e)(R_f))_h$—, an alkyl group, an aryl group, a heterocyclic ring, an arylheterocyclic ring, or —$(CH_2CH_2O)_q$—;

E at each occurrence is independently -T-, an alkyl group, an aryl group, —$(C(R_e)(R_f))_h$—, a heterocyclic ring, an arylheterocyclic ring, or —$(CH_2CH_2O)_q$—;

h is an integer form 1 to 10;

q is an integer of from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a carbamoyl, a urea, a nitro, -T-Q, or $(C(R_e)(R_f))_k$-T-Q, or $R_e$ and $R_f$ taken together with the carbon atom to which they are attached are a carbonyl, a methanthial, a heterocyclic ring, a cycloalkyl group or a bridged cycloalkyl group;

k is an integer from 1 to 3;

T at each occurrence is independently a covalent bond, a carbonyl, an oxygen, —S(O)$_o$— or —N($R_a$)$R_i$—;

o is an integer from 0 to 2;

$R_a$ is a lone pair of electrons, a hydrogen or an alkyl group;

$R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T-Q)($R_e$)($R_f$), or —(N$_2$O$_2$—)$^-$.M$^+$, wherein M$^+$ is an organic or inorganic cation; with the proviso that when $R_3$ is —CH$_2$—C(T-Q)($R_e$)($R_f$) or —(N$_2$O$_2$)$^-$.M$^+$, or $R_e$ or $R_f$ are T-Q or $(C(R_e)(R_f))_k$-T-Q, then the "-T-Q" subgroup designated in X can be a hydrogen, an alkyl, an alkoxy, an alkoxyalkyl, an aminoalkyl, a hydroxy, a heterocyclic ring or an aryl group.

2. The compound of claim 1, wherein the compound of Formula (I) is a nitrosated cimetidine, a nitrosylated cimetidine, a nitrosated and nitrosylated cimetidine, a nitrosated nizatidine, a nitrosylated nizatidine, a nitrosated and nitrosylated nizatidine, a nitrosated ranitidine, a nitrosylated ranitidine, a nitrosated and nitrosylated ranitidine, a nitrosated burimamide, a nitrosylated burimamide, a nitrosated and nitrosylated burimamide or a pharmaceutically acceptable salt thereof.

3. A composition comprising the compound of claim 1 and a pharmaceutically acceptable carrier.

4. The composition of claim 3, further comprising at least one of a nonsteroidal antiinflammatory drug, an antacid, a bismuth-containing reagent or an anti-viral agent.

5. A method for treating or preventing a gastrointestinal disorder, facilitating ulcer healing, or decreasing the recurrence of an ulcer in a patient in need thereof comprising administering to the patient a therapeutically effective amount of the composition of claim 3.

6. The method of claim 5, further comprising administering to the patient a therapeutically effective amount of an antacid.

7. The method of claim 5, wherein the gastrointestinal disorder is a peptic ulcer, gastric hyperacidity, dyspepsia, gastroparesis, Zollinger-Ellison syndrome, gastroesophageal reflux disease, a stress ulcer, a bleeding peptic ulcer, short bowel syndrome, or a hypersecretory state associated with systemic mastocytosis or basophilic leukemia and hyperhistaminemia.

8. A method for improving the gastroprotective properties, the anti-*Helicobacter* properties, or the antacid properties of an H$_2$ receptor antagonist comprising administering to a patient in need thereof a therapeutically effective amount of the composition of claim 3.

9. The method of claim 8, further comprising administering to the patient a therapeutically effective amount of a bismuth-containing reagent.

10. A method for improving the gastroprotective properties, the anti-*Helicobacter* properties or the antacid properties of an H$_2$ receptor antagonist compound comprising administering to a patient in need thereof a therapeutically effective amount of a bismuth complex of the composition of claim 3.

11. A method for decreasing or reversing gastrointestinal toxicity or facilitating ulcer healing resulting from administration of a nonsteroidal antiinflammatory drug to a patient comprising administering to a patient in need thereof a therapeutically effective amount of at least one nonsteroidal antiinflammatory drug and the composition of claim 3.

12. A method for treating an inflammation or a microbial infection in a patient in need thereof comprising administering to the patient a therapeutically effective amount of the composition of claim 3.

13. The method of claim 12, wherein the inflammation or microbial infection is in the eye, ear or nose of the patient or on the skin of the patient.

14. A method for treating or preventing an ophthalmic disease or disorder in a patient in need thereof comprising administering to the patient a therapeutically effective amount of the composition of claim 3.

15. The method of claim 14, wherein the ophthalmic disease or disorder is glaucoma, inflammation of the eye or elevation of intraocular pressure.

16. A method for treating multiple sclerosis in a patient in need thereof comprising administering to the patient a therapeutically effective amount of the composition of claim 3.

17. A method for treating a viral infection in a patient in need thereof comprising administering to the patient a therapeutically effective amount of the composition of claim 3.

18. The method of claim 17, further comprising administering to the patient a therapeutically effective amount of an anti-viral agent.

19. The method of claim 18, wherein the viral infection is HIV disease.

20. A composition comprising at least one compound of claim 1 or a pharmaceutically acceptable salt thereof, and at least one compound that donates, transfers or releases nitric oxide, or induces the production of endogenous nitric oxide or endothelium-derived relaxing factor, or is a substrate for nitric oxide synthase.

21. The composition of claim 20 further comprising a pharmaceutically acceptable carrier.

22. The composition of claim 20, wherein the compound that donates, transfers, or releases nitric oxide, or induces the production of endogenous nitric oxide or endothelium-derived relaxing factor or is a substrate for nitric oxide synthase is an S-nitrosothiol.

23. The composition of claim 22, wherein the S-nirrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

24. The composition of claim 22, wherein the S-nitrosothiol is:

(i) HS(C($R_e$)($R_f$))$_m$SNO;

(ii) ONS(C($R_e$)($R_f$))$_m$$R_e$; and (iii) H$_2$N—CH(CO$_2$H)—(CH$_2$)$_m$—C(O)NH—CH(CH$_2$SNO)—C(O)NH—CH$_2$—CO$_2$H;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxainido, a alkyl carboxamido, an aryl carboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a carbamoyl, a urea, a nitro, -T-Q, or $(C(R_e)(R_f))_k$-T-Q, or $R_e$ and $R_f$ taken together with the carbon atom to which they are attached are a carbonyl, a methanthial, a heterocyclic ring, a cycloalkyl group or a bridged cycloalkyl group; Q is —NO or —$NO_2$, and T is independently a covalent bond, a carbonyl, an oxygen, —$S(O)_o$— or —$N(R_a)R_j$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—C(T-Q)($R_e$)($R_f$), or —$(N_2O_2$—$)^-.M^+$, wherein $M^+$ is an organic or inorganic cation; with the proviso that when $R_i$ is —$CH_2$—C(T-Q)($R_e$)($R_f$) or —$(N_2O_2$—).$M^+$, then "-T-Q" can be a hydrogen, an alkyl group, an alkoxyalkyl group, an aminoalkyl group, a hydroxy group or an aryl group.

25. The composition of claim 20, wherein the compound that donates, transfers, or releases nitric oxide, or induces the production of endogenous nitric oxide or endothelium-derived relaxing factor, or is a substrate for nitric oxide synthase, is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine or glutamine.

26. The composition of claim 20, wherein the compound that donates, transfers, or releases nitric oxide, or induces the production of endogenous nitric oxide or endothelium-derived relaxing factor, or is a substrate for nitric oxide synthase is:
(i) a compound that comprises at least one ON—O—, ON—N— or ON—C— group;
(ii) a compound that comprises at least one $O_2N$—O—, $O_2N$—N—, $O_2N$—S— or —$O_2N$—C— group; or
(iii) a N-oxo-N-nitrosoamine having the formula: $R^1R^2N$—N(O—$M^+$)—NO, wherein $R^1$ and $R_2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation.

27. The composition of claim 26, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

28. The composition of claim 26, wherein the compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleohide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

29. The composition of claim 20, further comprising at least one of a nonsteroidal antiinflammatory drug, an antacid, a bismuth-containing reagent or an anti-viral agent.

30. A method for treating or preventing a gastrointestinal disorder, facilitating ulcer healing, or decreasing the recurrence of an ulcer in a patient in need thereof comprising administering to the patient a therapeutically effective amount of the composition of claim 20.

31. The method of claim 30, further comprising administering to the patient a therapeutically effective amount of an antacid.

32. The method of claim 30, wherein the gastrointestinal disorder is a peptic ulcer, gastric hyperacidity, dyspepsia, gastroparesis, Zollinger-Ellison syndrome, gastroesophageal reflux disease, a stress ulcer, a bleeding peptic ulcer, short bowel syndrome, or a hypersecretory state associated with systemic mastocytosis or basophilic leukemia and hyperhistaminemia.

33. A method for improving the gastroprotective properties, the anti-*Helicobacter* properties, or the antacid properties of an $H_2$ receptor antagonist comprising administering to a patient in need thereof a therapeutically effective amount of the composition of claim 20.

34. The method of claim 33, further comprising administering to the patient a therapeutically effective amount of a bismuth-containing reagent.

35. A method for improving the gastroprotective properties, the anti-*Helicobacter* properties or the antacid properties of an $H_2$ receptor antagonist compound comprising administering to a patient in need thereof a therapeutically effective amount of a bismuth complex of the composition of claim 20.

36. A method for decreasing or reversing gastrointestinal toxicity or facilitating ulcer healing resulting from administration of a nonsteroidal antiinflammatory drug to a patient comprising administering to a patient in need thereof a therapeutically effective amount of at least one nonsteroidal antiinflammatory drug and the composition of claim 20.

37. A method for treating an inflammation or a microbial infection in a patient in need thereof comprising administering to the patient a therapeutically effective amount of the composition of claim 20.

38. The method of claim 37, wherein the inflammation or microbial infection is in the eye, ear or nose of the patient or on the skin of the patient.

39. A method for treating or preventing an ophthalmic disease or disorder in a patient in need thereof comprising administering to the patient a therapeutically effective amount of the composition of claim 20.

40. The method of claim 39, wherein the ophthalmic disease or disorder is glaucoma, inflammation of the eye or elevation of intraocular pressure.

41. A method for treating multiple sclerosis in a patient in need thereof comprising administering to the patient a therapeutically effective amount of the composition of claim 20.

42. A method for treating a viral infection in a patient in need thereof comprising administering to the patient a therapeutically effective amount of the composition of claim 20.

43. The method of claim 42, further comprising administering to the patient a therapeutically effective amount of an anti-viral agent.

44. The method of claim 42, wherein the viral infection is HIV disease.

45. A kit comprising at least one compound of claim 1 or a pharmaceutically acceptable salt thereof.

46. The kit of claim 45, further comprising at least one compound that donates, transfers or releases nitric oxide, induces the production of endogenous nitric oxide or endothelium-derived relaxing factor, or is a substrate for nitric oxide synthase, a nonsteroidal antiinflammatory drug, an antacid, a bismuth-containing reagent or an anti-viral agent.

47. The kit of claim 45, wherein the compound of claim 1 and the at least one compound that donates, transfers or releases nitric oxide, induces the production of endogenous nitric oxide or endothelium-derived relaxing factor, or is a substrate for nitric oxide synthase, a nonsteroidal antiinflammatory drug, an antacid, a bismuth-containing reagent or an anti-viral agent are in the form of separate components in the kit.

48. A kit comprising the composition of claim 20 or 28.

* * * * *